US011721415B2

(12) United States Patent
Noro et al.

(10) Patent No.: US 11,721,415 B2
(45) Date of Patent: Aug. 8, 2023

(54) MEDICAL INFORMATION SYSTEM, INFORMATION PROCESSING TERMINAL, MEDICAL INFORMATION SERVER AND MEDICAL INFORMATION PROVIDING METHOD

(71) Applicant: Toshiba Medical Systems Corporation, Otawara (JP)

(72) Inventors: Kazumasa Noro, Otawara (JP); Kousuke Sakaue, Nasushiobara (JP); Masahiro Ozaki, Otawara (JP); Kazuki Utsunomiya, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 921 days.

(21) Appl. No.: 15/665,928

(22) Filed: Aug. 1, 2017

(65) Prior Publication Data
US 2018/0039739 A1 Feb. 8, 2018

(30) Foreign Application Priority Data

Aug. 2, 2016 (JP) .................. 2016-152237
Jul. 31, 2017 (JP) .................. 2017-147571

(51) Int. Cl.
*G16H 10/60* (2018.01)
*G06F 40/30* (2020.01)
(Continued)

(52) U.S. Cl.
CPC ............. *G16H 10/60* (2018.01); *G06F 40/30* (2020.01); *G10L 15/26* (2013.01); *H04L 67/535* (2022.05); *G16H 50/30* (2018.01); *H04L 67/52* (2022.05)

(58) Field of Classification Search
CPC .. G06Q 50/22–24; G16H 10/60; G16H 50/30; G10L 15/26; G06F 40/30; H04L 67/22; H04L 67/18
See application file for complete search history.

(56) References Cited

U.S. PATENT DOCUMENTS 6,230,121 B1    5/2001  Weber
8,346,864 B1 *  1/2013  Amidon .................. G06Q 50/01
                                                             709/204
(Continued)

FOREIGN PATENT DOCUMENTS

CN    100370414 C  *  2/2008  ......... G06K 9/00335
JP    09-053957        2/1997
(Continued)

OTHER PUBLICATIONS

Ali, Tauhid. "Validation of Patient-Reported Outcomes in Parkinson's Disease : Comparisons of Generic and Disease-Specific Health-Related Quality of Life Instruments." Order No. U584151 Cardiff University (United Kingdom), 2005. Ann Arbor: ProQuest. Web. Mar. 14, 2023. (Year: 2005).*

*Primary Examiner* — Lena Najarian
(74) *Attorney, Agent, or Firm* — Oblon, McClelland, Maier & Neustadt, L.L.P.

(57) ABSTRACT

According to one embodiment, a medical information system comprises processing circuitry. The processing circuitry collects social behavior information about a measurement target person. The processing circuitry identifies a social relationship between the measurement target person and others, and a behavior pattern of the measurement target person, by using the collected social behavior. The processing circuitry quantitatively measures a sociality item of the measurement target person by using the identified social relationship and the identified behavior pattern.

12 Claims, 33 Drawing Sheets

(51) Int. Cl.
  *G10L 15/26* (2006.01)
  *H04L 67/50* (2022.01)
  *G16H 50/30* (2018.01)
  *H04L 67/52* (2022.01)

(56) References Cited

U.S. PATENT DOCUMENTS

| | | | |
|---|---|---|---|
| 8,825,777 B2* | 9/2014 | DeLuca | G06Q 50/01 |
| | | | 709/206 |
| 9,313,325 B2* | 4/2016 | Ueno | H04M 11/025 |
| 9,799,080 B2* | 10/2017 | Lee | G06Q 50/01 |
| 10,083,415 B2* | 9/2018 | Hale | G06F 16/285 |
| 2006/0026036 A1* | 2/2006 | Mahmood | G06Q 10/04 |
| | | | 705/2 |
| 2012/0296642 A1* | 11/2012 | Shammass | G10L 25/63 |
| | | | 704/211 |
| 2013/0012790 A1 | 1/2013 | Horseman | |
| 2013/0101264 A1 | 4/2013 | Vermeulen et al. | |
| 2016/0188821 A1* | 6/2016 | Ozeran | G16H 50/20 |
| | | | 705/3 |
| 2017/0061965 A1* | 3/2017 | Penilla | G06K 9/00845 |

FOREIGN PATENT DOCUMENTS

| | | |
|---|---|---|
| JP | 3277172 | 4/2002 |
| JP | 2004-234410 | 8/2004 |
| JP | 4353940 | 10/2009 |
| JP | 2013-535660 | 9/2013 |
| JP | 2013-206320 | 10/2013 |
| JP | 2014-524797 | 9/2014 |
| WO | WO 2013/008673 A1 | 1/2013 |

* cited by examiner

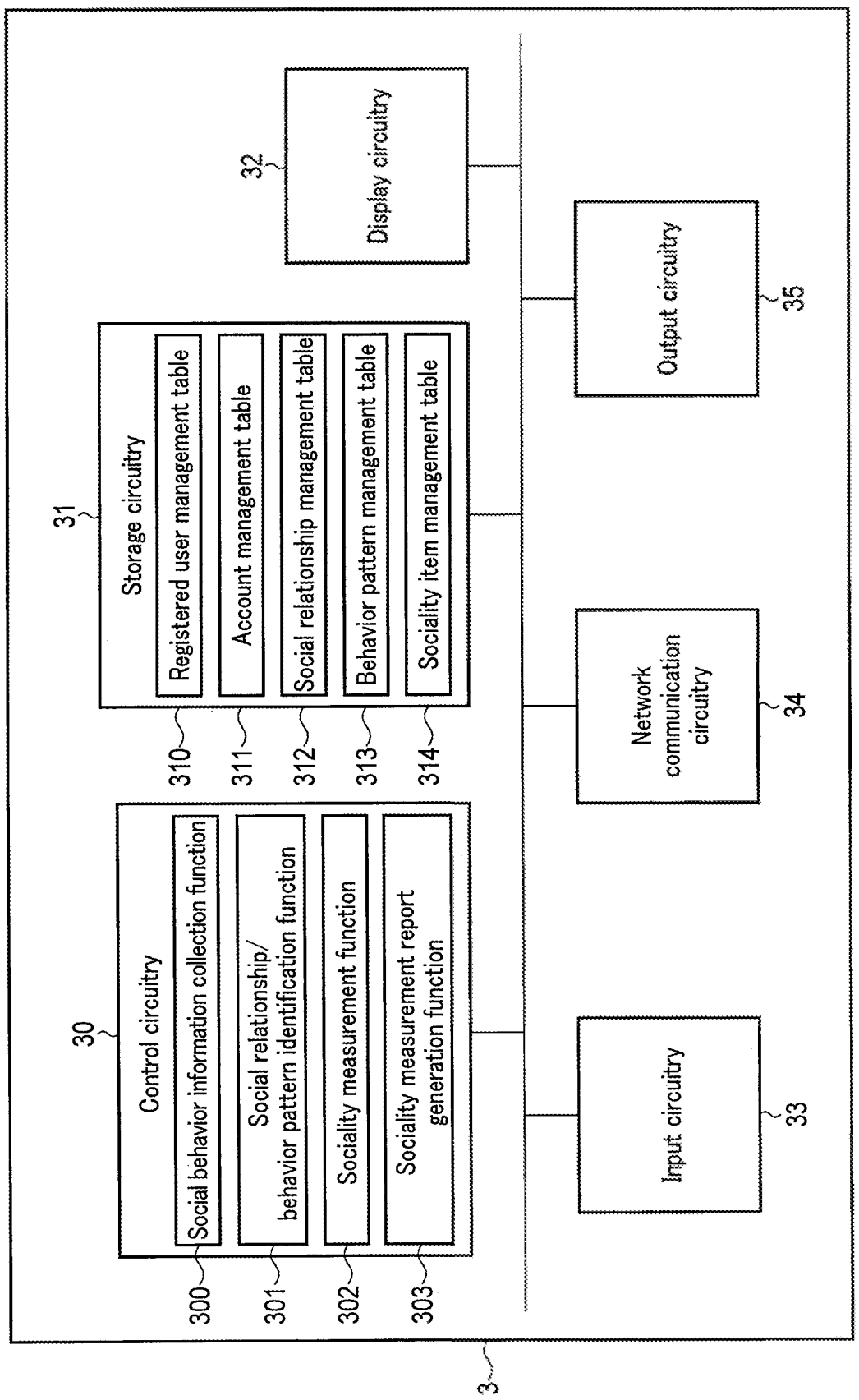
F I G. 3

| Registration unit | Name |
|---|---|
| U00001 | Taro Tokkyo |
| U00002 | Hanako Jitsuan |
| : | : |
| U00000 | Unknown |

FIG. 4

| Registration number | Account type | Account information | Access schedule for account |
|---|---|---|---|
| U00001 | Phone number | 090-1234-5678 | CycleT$_1$ |
| U00001 | GPS | AABBCC0123 | CycleT$_2$ |
| U00001 | Email address | taro_tokkyo@tokkyo.co.jp | CycleT$_3$ |
| U00002 | Phone number | 080-9876-5432 | CycleT$_1$ |
| U00002 | Email address | hanako_j@webmail.com | CycleT$_3$ |
| U00002 | GPS | DDEEFF9876 | CycleT$_2$ |
| U00002 | SNS | HT0123 | CycleT$_4$ |
| U00002 | Proximity communication number | AABBCC0123 | CycleT$_5$ |
| ⋮ | ⋮ | ⋮ | ⋮ |

F I G. 5

| Social relationship registration number | Social behavior originator registration number | Social behavior receiver registration number | Social relationship identification number |
|---|---|---|---|
| R00001 | U00001 | U00002 | RE10(Friend) |
| R00002 | U00001 | U00003 | RE1(Parent) |
| R00003 | U00001 | U00004 | RE0(Unrelated person) |
| R00004 | U00002 | U00001 | RE10(Friend) |
| R00005 | U00002 | U00005 | RE12(Acquaintance) |
| R00006 | U00003 | U00001 | RE2(Child) |
| .. | .. | .. | .. |

FIG. 6

| Social relationship Identification number | Social relationship | Social relationship weight |
|---|---|---|
| RE1 | Parent | 4 |
| RE2 | Child | 4 |
| RE3 | Grandchild | 4 |
| RE4 | Wife | 4 |
| ⋮ | ⋮ | ⋮ |
| RE10 | Friend | 3 |
| RE11 | Fellow | 3 |
| RE12 | Acquaintance | 2 |
| RE0 | Unrelated person | 1 |

F I G. 7

| Behavior pattern identification number | Behavior pattern |
|---|---|
| AC1 | Visit |
| AC2 | Meet |
| AC3 | Show affection |
| AC4 | Socialize |
| AC5 | Worry about health |
| AC6 | Talk |
| AC7 | Request |
| AC8 | Yell |
| AC9 | Have interest in problem of others |
| ⋮ | |
| AC0 | None |

F I G. 8

| Behavior pattern identification number | Determination reference text |
|---|---|
| AC3 | Like |
| AC3 | Love |
| AC3 | Miss |
| AC4 | Play |
| AC4 | Drink |
| AC5 | Tired |
| AC5 | Cannot sleep |
| AC7 | Please |
| : | : |

F I G. 9

SI (Social cooperativity)
1: Number of visits to others is decreasing.
2: I do not visit someone's house at all.
3: I rarely have interest in problem of others. For example, even if someone talks to me about his/her problem, I have no will to listen to or support him/her.
4: I am apt to get irritated by people or things around me, and I often vent my anger, snarl, or criticize.
5: I rarely show affection.
6: I am breaking away from socialization with fellows.
7: Number of visits to friends is decreasing.
8: I am avoiding social visits by other people.
9: I am breaking away from sexual relations.
10: I often worriedly say if I am healthy.

F I G. 10

| Sociality item number | Sociality item contents | Social relationship to be referred to | Behavior pattern to be referred to |
|---|---|---|---|
| S1 | Number of visits to friends is decreasing. | Social relationship identification number=RE10 | AC1 |
| S2 | I try to stay away from my family as much as possible. | Social relationship weight=4 | AC1 |
| S3 | I often worriedly say if I am healthy. | Social relationship weight≧1 | AC5 |
| S4 | I rarely talk to people around me nowadays. | Social relationship weight≧3 | AC6 |
| S5 | I am breaking away from socialization with fellows. | Social relationship identification number=RE11 | AC4 |
| ⋮ | ⋮ | ⋮ | ⋮ |

FIG. 11

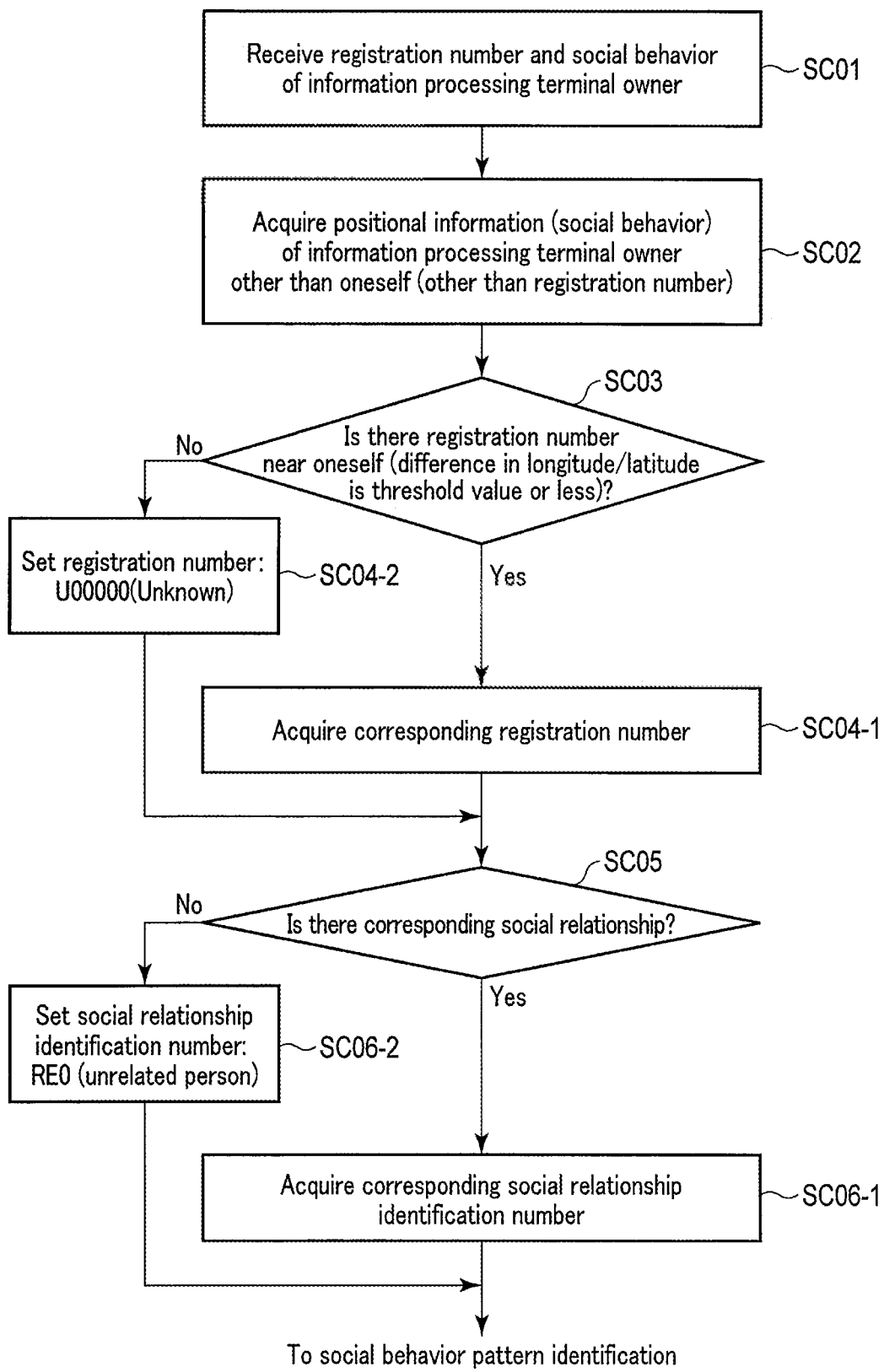
F I G. 14

| Relationship /behavior pattern recognition number | Registration number | Social relationship recognition receiver registration number | Social relationship identification number | Behavior pattern identification number | Social behavior occurrence time |
|---|---|---|---|---|---|
| RA00001 | U00001 | U00002 | RE10 | AC1 | 2015/12/4 10:00:00 |
| RA00002 | U00001 | U00005 | RE12 | AC1 | 2015/12/4 11:30:10 |
| RA00003 | U00001 | U00002 | RE10 | AC4 | 2015/12/4 11:00:00 |
| RA00004 | U00001 | U00002 | RE10 | AC5 | 2015/12/4 11:00:00 |
| RA00005 | U00002 | U00001 | RE10 | AC0 | 2015/12/5 13:00:00 |
| RA00006 | U00003 | U00004 | RE0 | AC6 | 2015/12/5 14:00:00 |
| RA00007 | U00001 | U00000 | RE0 | AC5 | 2015/12/6 15:00:00 |
| .. | .. | .. | .. | .. | .. |

FIG. 16

| Relationship/ behavior pattern recognition number | Social behavior originator registration number | Social behavior receiver registration number | Social relationship identification number | Social relationship weight | Acquisition date and time | Behavior pattern identification number |
|---|---|---|---|---|---|---|
| RA00001 | U00001 | U00002 | RE10 | 3 | 2015/12/1 10:00:00 | AC1 |
| RA00002 | U00001 | U00005 | RE12 | 2 | 2015/12/2 11:30:10 | AC1 |
| RA00003 | U00001 | U00002 | RE10 | 3 | 2015/12/4 11:00:00 | AC4 |
| RA00004 | U00001 | U00002 | RE10 | 3 | 2015/12/4 11:00:00 | AC5 |
| .. | .. | .. | .. | .. | .. | .. |

F I G. 18

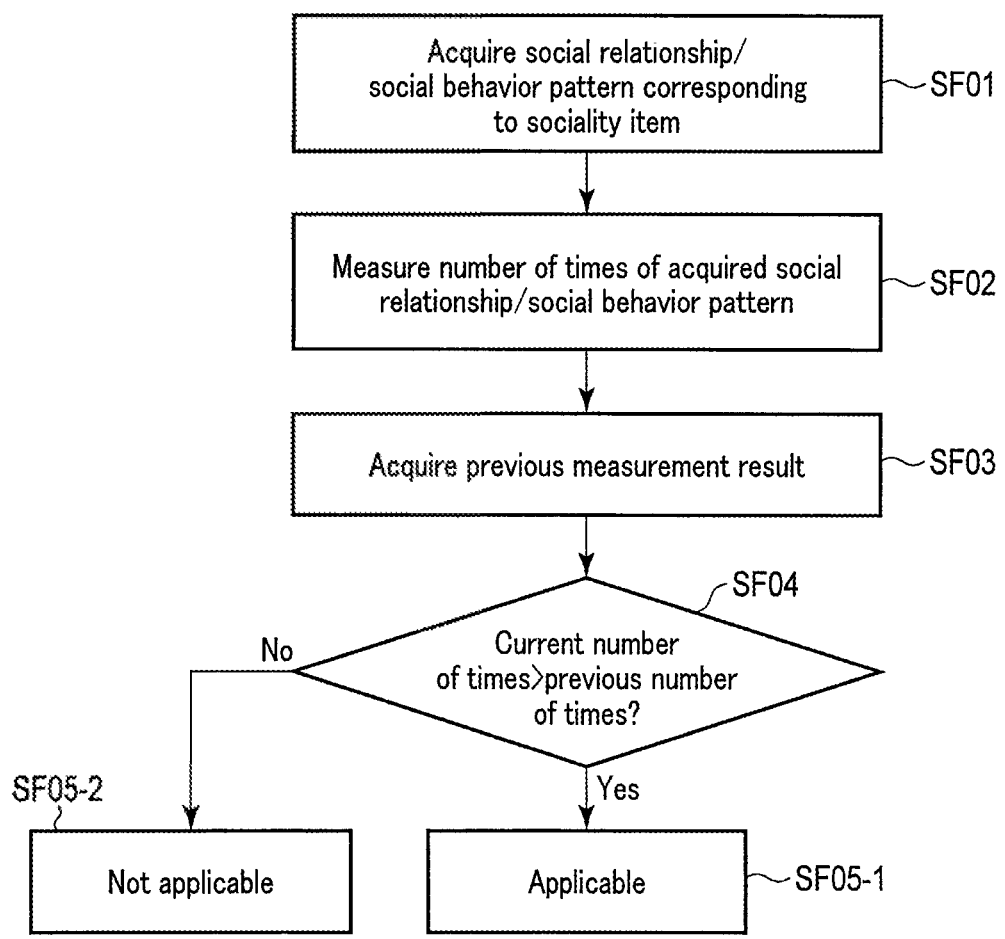
F I G. 19

| Registration number | Sociality item number | Measurement period | Number of times | Applicability |
|---|---|---|---|---|
| U00001 | S1 | 2015/11/1-2015/11/7 | 70 | Not applicable |
| U00001 | S3 | 2015/11/1-2015/11/7 | 15 | Not applicable |
| U00001 | S1 | 2015/11/8-2015/11/14 | 70 | Not applicable |
| U00001 | S1 | 2015/11/24-2015/11/30 | 20 | Applicable |
| U00001 | S2 | 2015/12/01-2015/12/7 | 10 | Applicable |
| .. | .. | .. | .. | .. |

F I G. 20

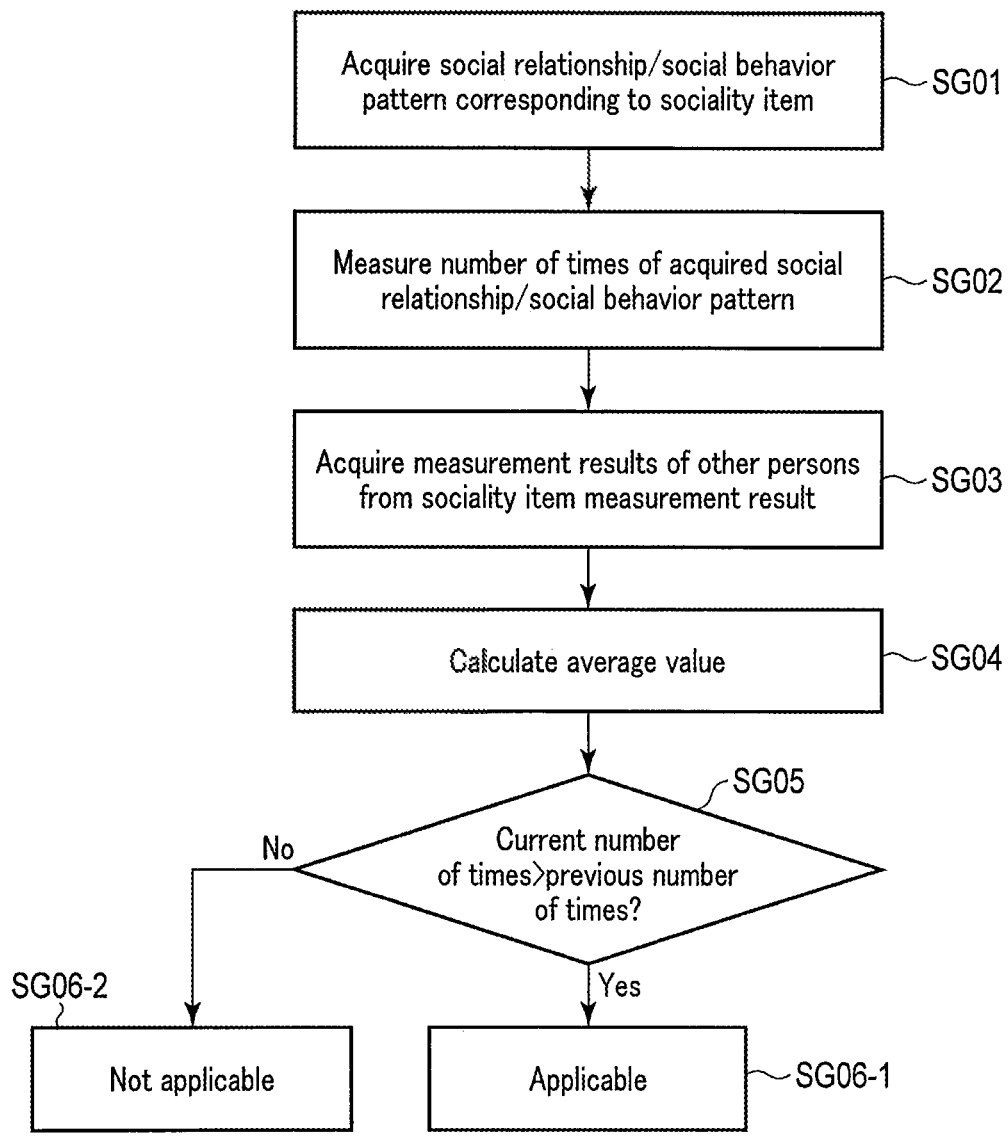
F I G. 21

QOL measurement result  Measurement index:SIP,Measurement period:(Start)yyyyMMdd-(End)yyyyMMdd Target person:

| Registration number | Name |
|---|---|
| U00001 | Taro Tokkyo |

Each score:

| | | | Applicability | Detailed information |
|---|---|---|---|---|
| SIP– Psychosocial Psychosocial region | SI/Social cooperativity | SI-1 Number of visits to friends is decreasing. | Applicable | See here for details |
| | | | | |
| | | | | |
| | | | | |

Total score:
xxxxxxxxxxxxxxxxxxxxxxxxxxxxxxxxxxxxxxxxxxxxxxxxx
xxxxxxxxxxxxxxxxxxxxxxxxxxxxxxxxxxxxxxxxxxxxxxxxx

F I G. 22A

QOL measurement result   Measurement index: SIP, Measurement period: (Start)yyyyMMdd-(End)yyyyMMdd Target person:

| Registration number | Name |
|---|---|
| D00001 | ○○○ |

Each score:

| | | | Number of applicabilities | Detailed information |
|---|---|---|---|---|
| SIP– Psychosocial Psychosocial region | SI/Social cooperativity | SI-1 | | |
| | | Number of visits to friends is decreasing | 6/20 | See here for details |
| | | | | |
| | | | | |
| | | | | |

Total score:
xxxxxxxxxxxxxxxxxxxxxxxxxxxxxxxxxxxxxxxxxxxxx
xxxxxxxxxxxxxxxxxxxxxxxxxxxxxxxxxxxxxxxxxxxxx

F I G. 22B

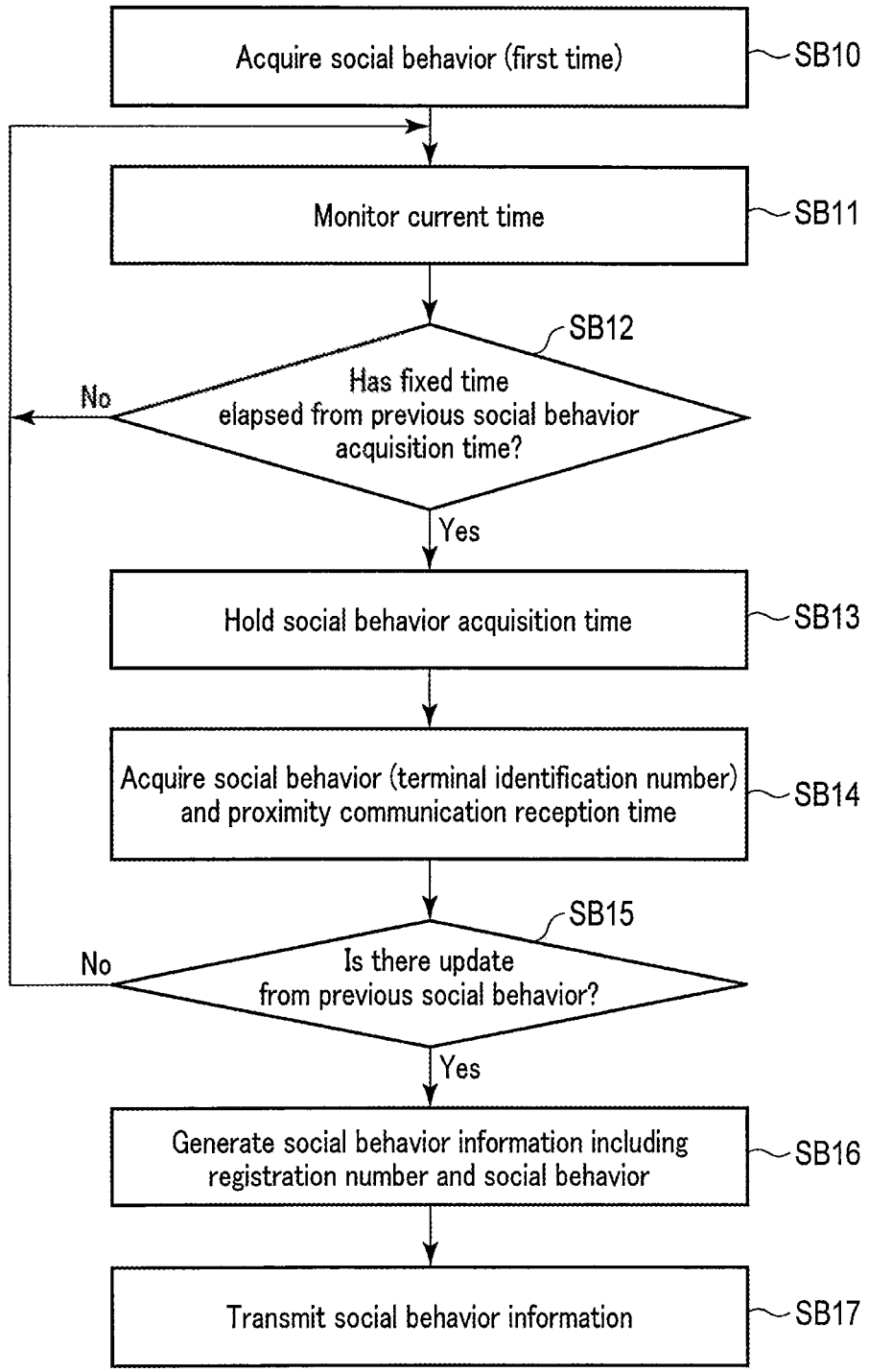
F I G. 23

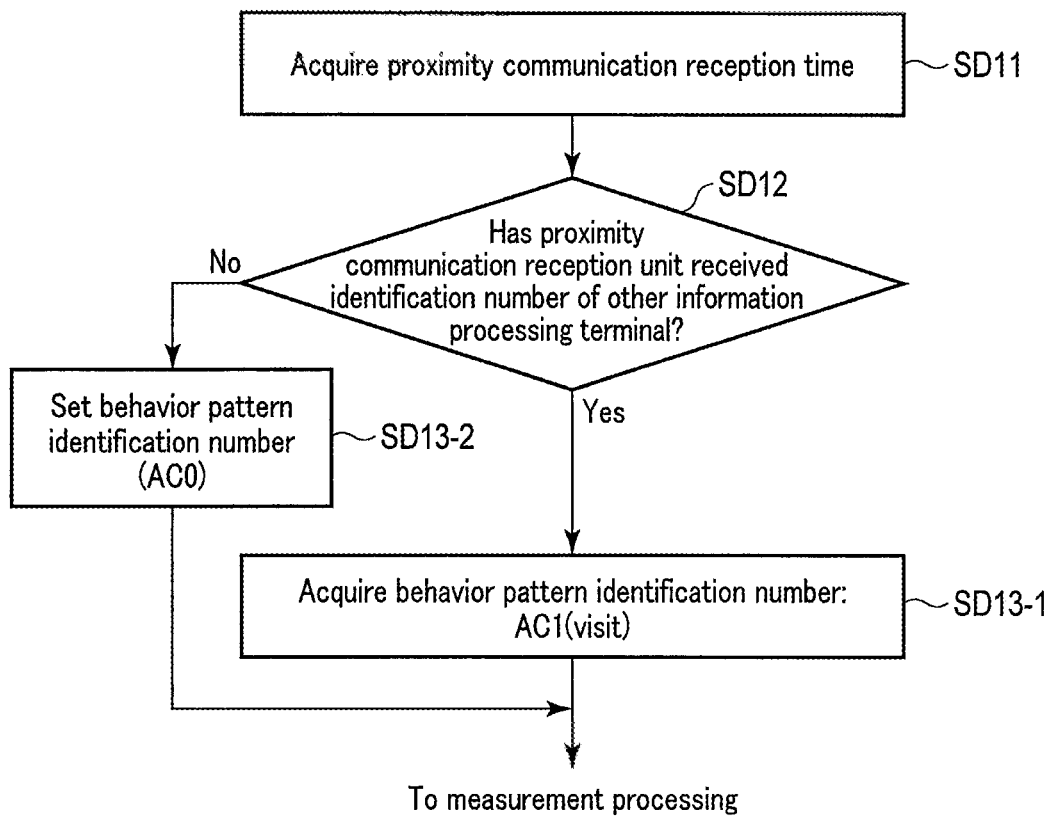
F I G. 25

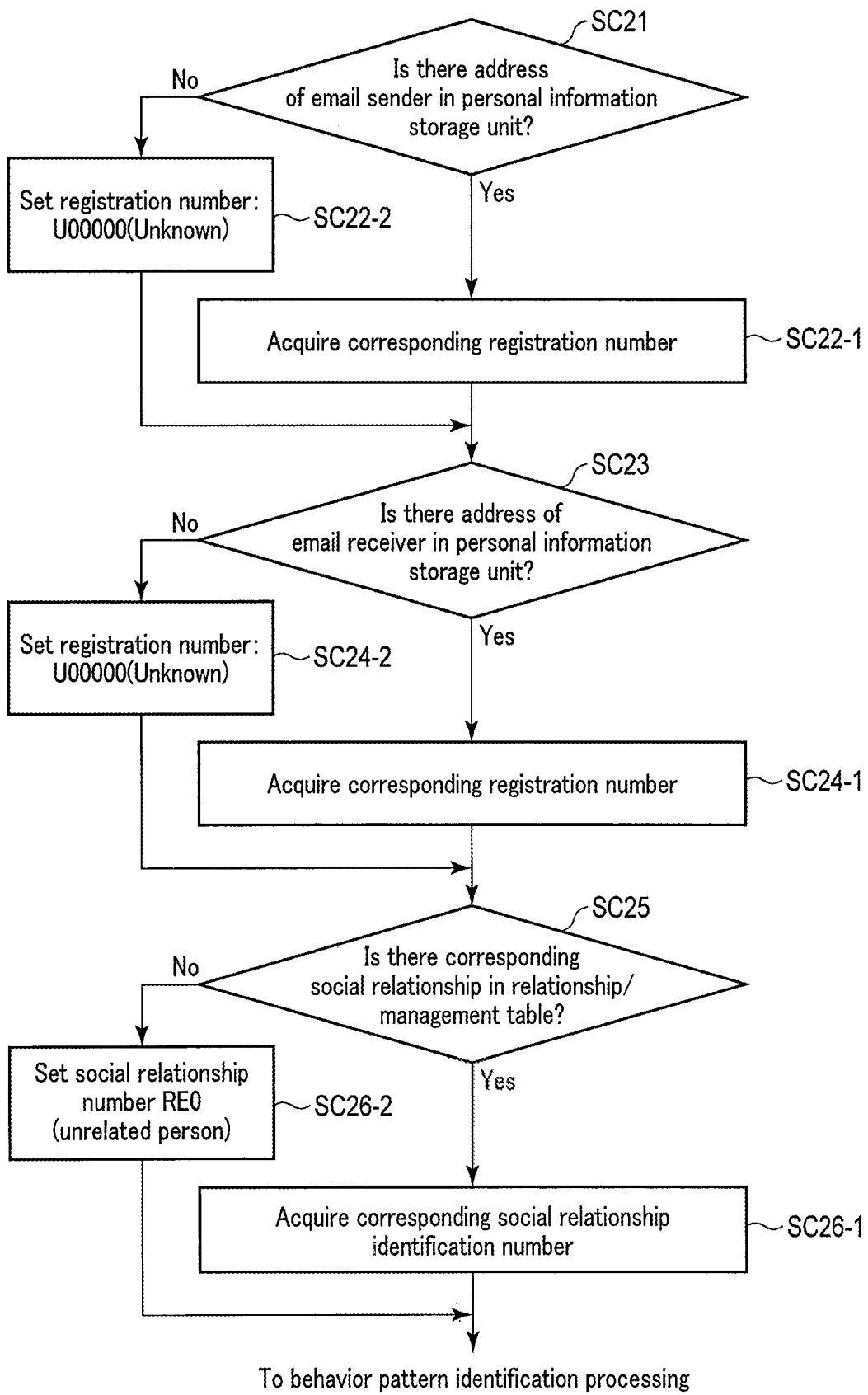
F I G. 27

MEDICAL INFORMATION SYSTEM, INFORMATION PROCESSING TERMINAL, MEDICAL INFORMATION SERVER AND MEDICAL INFORMATION PROVIDING METHOD

CROSS-REFERENCE TO RELATED APPLICATIONS

This application is based upon and claims the benefit of priority from the prior Japanese Patent Applications No. 2016-152237, filed Aug. 2, 2016 and No. 2017-147571, filed Jul. 31, 2017, the all of entire contents of which are incorporated herein by reference.

FIELD

Embodiments described herein relate generally to a medical information system, an information processing terminal, a medical information server and a medical information providing method.

BACKGROUND

In general, QOL (quality of life) is a concept to comprehend as a standard for evaluation as to whether or not a certain person lives a life like human beings, lives a life he wants, and finds happiness in his life. In recent years, this QOL attracts attention as evaluation indexes of medical practice. As typical indexes of the QOL, there are known SF-36 (medical outcome study 36 item short form health survey), SIP (sickness impact profile) and others. Furthermore, in such typical QOL indexes, an attempt of measurement concerning the indexes has begun in a physical field and other fields.

For example, in the SIP, as QOL indexes concerning sociality (sociality QOL indexes), there has been suggested the measurement of four categories of social cooperativity, communication, changes in behavior and emotional behavior. Heretofore, in case of measuring such sociality QOL indexes, information is acquired in a manner that a target person answers a questionnaire by himself, and index values are calculated based on this information.

However, the above-described conventional technique has, e.g., the following problem. That is, since answering the questionnaire is necessary, conscious effort is required, which is a burden on the target person. Furthermore, since the target person performs self-declaration himself/herself, objectivity lacks in some situations. Moreover, the indexes are evaluated irregularly, a change in physical status or a change in psychological status cannot be monitored in some situations.

Additionally, for example, in an evaluation of sleep and rest, a depth of sleep is accurately measured with an accuracy of 70% or more. Measuring the sociality QOL indexes with an equivalent accuracy is demanded.

BRIEF DESCRIPTION OF THE DRAWINGS

FIG. 3 is a block diagram of an external server 3;
FIG. 4 is a view showing an example of a registered measurement target person management table 310;
FIG. 5 is a view showing an example of an account management table 311;
FIG. 6 is a view showing an example of a social relationship management table 312;
FIG. 7 is a view showing an example of a relationship weight table;
FIG. 8 is a view showing an example of a behavior pattern management table 313;
FIG. 9 is a view showing an example of the behavior pattern management table 313 in case of using text data in, e.g., an email;
FIG. 10 is a view showing sociality QOL indexes conforming to SIP;
FIG. 11 is a view showing an example of a sociality item management table 314;
FIG. 14 is a view showing a flow of social relationship identification processing in the external server 3;
FIG. 16 is a view showing an example of a relationship/behavior pattern management table as a history over a predetermined period;
FIG. 18 is a view showing a relationship/behavior pattern management table about a measurement target person "registration number U00001" over a predetermined period;
FIG. 19 is a flowchart showing a flow of evaluation processing about a sociality item "S1 (number of visits to friends is decreasing)" at a step SE03;
FIG. 20 is a view showing an example of sociality measurement results acquired over a predetermined period;
FIG. 21 is a flowchart showing a flow of processing to evaluate the sociality item "S1 (number of visits to friends is decreasing)" by a comparison with a reference value provided by statistical processing;
FIG. 22A shows an example of a generated sociality measurement report;
FIG. 22B shows an example of a sociality measurement report generated when a statistical reference is used;
FIG. 23 is a flowchart showing a flow of social behavior automatic acquisition, social behavior information automatic generation, and automatic transmission processing in the information processing terminal 2 using proximity communication;
FIG. 25 is a view showing a flow of social behavior pattern identification processing according to Modification 1;
FIG. 27 is a view showing a flow of social relationship identification processing according to Modification 2;

DETAILED DESCRIPTION

Figure 1:
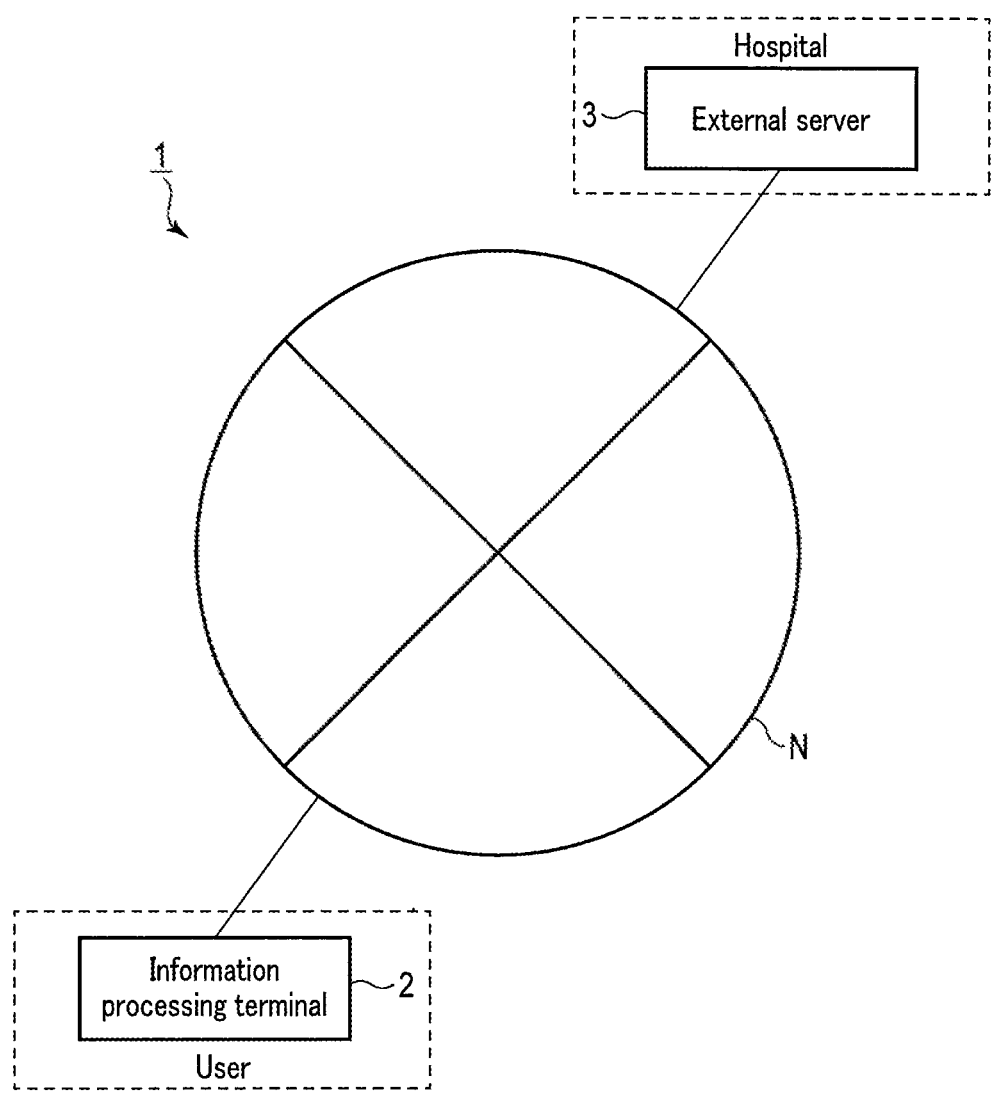
FIG. 1 is a schematic view of a medical information system 1.

According to one embodiment, a-medical information system comprises processing circuitry. The processing circuitry collects social behavior information about a measurement target person. The processing circuitry identifies a social relationship between the measurement target person and others, and a behavior pattern of the measurement target person, by using the collected social behavior. The processing circuitry quantitatively measures a sociality item of the measurement target person by using the identified social relationship and the identified behavior pattern.

First Embodiment

A medical information system according to this embodiment will now be described hereinafter with reference to the drawings. It is to be noted that like reference numerals denote constituent elements having substantially the same functions and structures, and an overlapping description will be given only when required.

FIG. 1 is a schematic view of a medical information system 1. As shown in the drawing, the medical information system 1 comprises an information processing terminal 2 and an external server 3 which can be connected to the information processing terminal 2 through a network. Configurations of the information processing terminal 2 and the external server 3 will now be described hereinafter in detail.

(Information Processing Terminal 2)

The information processing terminal 2 is owned by a person who is a target of sociality measurement (a measurement target person) using this medical information system 2, detects information concerning social behavior of the measurement target person at predetermined timing, and transmits it to the external server 3 through the network. The information processing terminal 2 can be realized by implementing a dedicated application in, e.g., a mobile phone such as a smartphone or an information device such as a wearable terminal or a tablet terminal. However, the information processing terminal 2 may be realized by using a dedicated information device without being restricted to this example.

Figure 2:
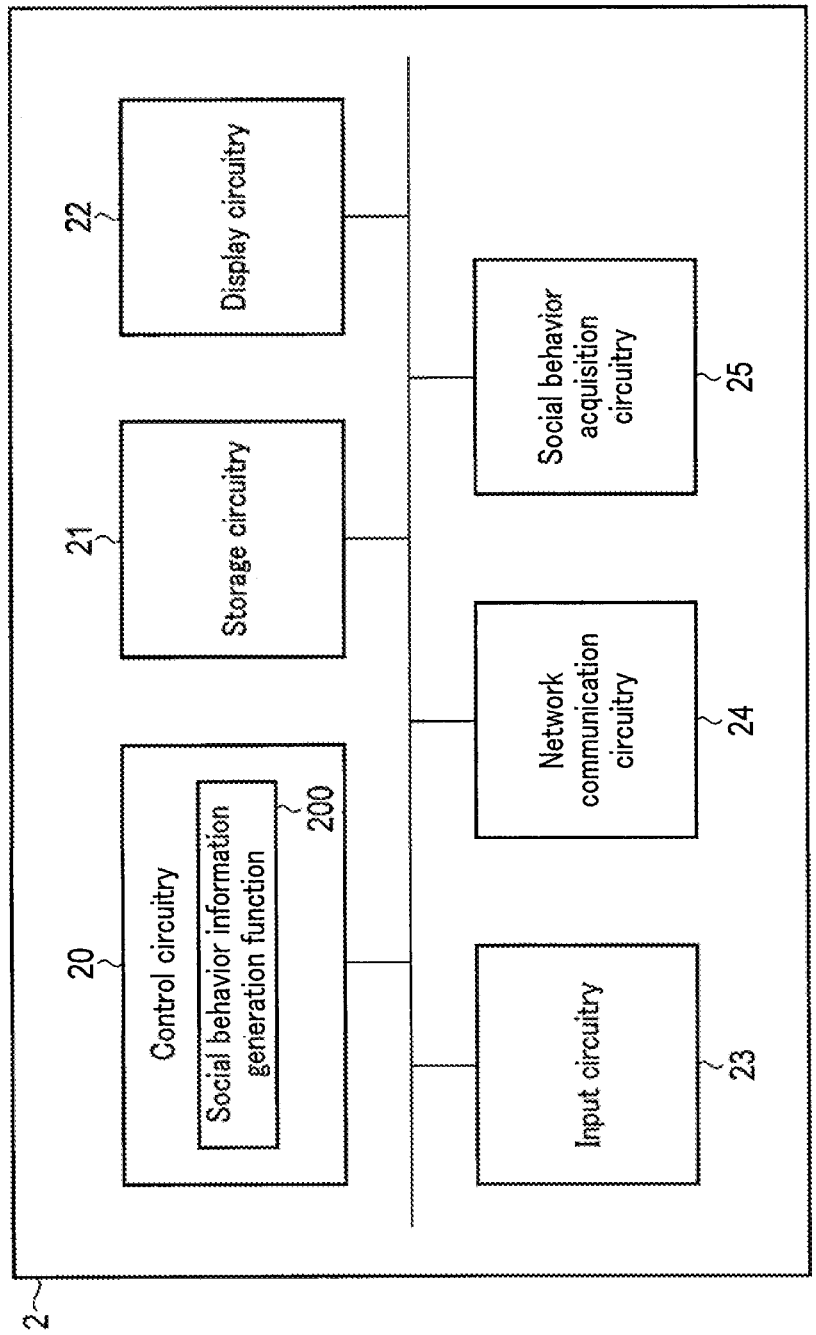
FIG. 2 is a block diagram of an information processing terminal 2.

FIG. 2 is a block diagram of the information processing terminal 2. As shown in the drawing, the information processing terminal 2 comprises control circuitry 20, storage circuitry 21, display circuitry 22, input circuitry 23, network communication circuitry 24, and social behavior acquisition circuitry 25.

The control circuitry 20 is a processor such as a CPU which integrally controls the information processing terminal 2. Further, the control circuitry 20 starts up a dedicated program stored in the storage circuitry 21 to realize a function as a social behavior information generation function 200. This social behavior information generation function 200 generates social behavior information about a measurement target person who owns the information processing terminal 2 at predetermined timing. Specific processing executed by the social behavior information generation function 200 will be described later in detail.

The storage circuitry 21 is a storage medium or the like such as a magnetic or optical recording medium, a semiconductor memory, or the like which can be read by a processor, and sequentially stores the dedicated program to realize the social behavior information generation function 200 and social behavior information generated by the social behavior information generation function 200. Furthermore, the storage circuitry 21 stores a program for network communication, a program for GPS communication, and the like.

The display circuitry 22 is a display, and displays a GUI for various kinds of operations, a later-described sociality measurement report, or the like as required. The input circuitry 21 is realized by, e.g., a mouse, a numerical keypad, a keyboard, a touch pad through which an instruction is input when an operation surface is touched, and the like. The input circuitry 23 accepts various kinds of instructions from the measurement target person. The input circuitry 23 is connected to the control circuitry 20 through a bus, converts an operation instruction input from the measurement target person into an electrical signal, and outputs the electrical signal to the control circuitry 20. It is to be noted that, in this embodiment, the input circuitry 23 is not restricted only to input circuitry including physical operation components, e.g., the mouse or the numerical keypad. For example, an electrical signal processing circuit which receives an electrical signal corresponding to an operation instruction input from an external input device provided separately from the information processing terminal 2 and outputs this electrical signal to the control circuitry 20 is also included in the example of the input circuitry 23.

The network communication circuitry 24 transmits or receives data to or from the external server 3 through the network N. In particular, in processing which follows a later-described sociality measurement function, the sociality behavior information generated by the sociality behavior information generation function 200 is transmitted to the external server 3 through the network N.

The social behavior acquisition circuitry 25 acquires social behavior of the measurement target person wearing the information processing terminal 2. Here, the social behavior of the measurement target person is information acquired through the information processing terminal 2 to measure social cooperativity, communication, changes in behavior, and emotional behavior, and the like, and it is, e.g., a current position of the measurement target person wearing the information processing terminal 2, contents of a conversation, communication contents in a document such as an email, an amount of exercise, and the like. To give a specific description, a current position (degrees of latitude and longitude and the like at a present time) of the measurement target person wearing the information processing terminal 2 provided by communication with a GPS will be described as social behavior hereinafter. It is to be noted that the social behavior acquisition circuitry 25 may have a microphone to collect daily sound of the measurement target person, an acceleration sensor to measure a daily amount of exercise of the measurement target person or the like.

(External Server 3)

The external server 3 is installed on a side of a person who performs sociality measurement (e.g., a hospital or a support provider; a hospital is taken as an example in this embodiment), and transmits or receives data to or from the information processing terminal 2 owned by the measurement target person through the network N.

FIG. 3 is a block diagram of the external server 3. As shown in the drawing, the external server 3 comprises control circuitry 30, storage circuitry 31, display circuitry 32, input circuitry 33, network communication circuitry 34, and an output circuitry 35.

The control circuitry 30 is a processor such as a CPU which integrally controls the external server 3. Furthermore, the control circuitry 30 starts up a dedicated program stored in the storage circuitry 31 to realize functions as a social behavior information collection function 300, a social relationship/social behavior pattern identification function 301, a sociality measurement function 302, and a sociality measurement report generation function 303. The social behavior information collection function 300 collects social behavior information sequentially transmitted from the information processing terminal 2 owned by each measurement target person. The social relationship/social behavior pattern identification function 301 executes social relationship identification processing and social behavior pattern identification processing on the basis of the social behavior information collected by the social behavior information collection function 300. The sociality measurement function 302 quantitatively measures sociality on the basis of a social relationship and a social behavior pattern identified by the social relationship/social behavior pattern identification function 301. The sociality measurement report generation function 303 generates a sociality measurement report on the basis of measurement results provided by the sociality measurement function 302. Specific processing executed by the social behavior information collection function 300, the social relationship/social behavior pattern identification function 301, the sociality measurement function 302, and the sociality measurement report generation function 303 will be described later in detail.

The storage circuitry 31 is a storage medium or the like such as a magnetic or optical recording medium, a semiconductor memory, or the like which can be read by a processor, and stores dedicated programs to realize the social behavior information collection function 300, the sociality measurement function 302, and the sociality measurement report generation function 303, the sociality behavior information about each measurement target person collected by the social behavior information collection function 300, the measurement results of the sociality measurement function 302, and the sociality measurement report generated by the sociality measurement report generation function 303.

Moreover, the storage circuitry 21 stores a registered measurement target person management table 310, an account management table 311, a social relationship management table 312, a behavior pattern management table 313, and a sociality item management table 314. These various kinds of tables are used in processing which follows the sociality measurement function. Contents of each table will now be described hereinafter.

FIG. 4 is a view showing an example of the registered measurement target person management table 310. As shown in the drawing, the registered measurement target person management table 310 is a management table in which each measurement target person is associated with a unique registration number. When each measurement target person carries out measurement target person registration in this medical information system 1 in advance to acquire a unique registration number, the registration target person's name and the corresponding registration number are managed by the registration measurement target person management table 310.

FIG. 5 is a view showing an example of the account management table 311. In the account management table 311, account information of communication means used in acquisition of the social behavior information is registered for each measurement target person, and an access schedule for each account is stored in association with this information. It is to be noted that each measurement target person can register account types and register pieces of account information for each account type. When the pieces of account types and account information are used in this manner, the social behavior information of the corresponding measurement target person (the measurement target person) can be acquired from various daily circumstances.

FIG. 6 is a view showing an example of the social relationship management table 312. As shown in the drawing, in the social relationship management table 312, social relationships between measurement target persons registered in the medical information system 1 are associated, and relationships of a specific measurement target person to other measurement target persons are defined. Here, assuming that a measurement target person him/herself is a "social behavior originator" and another measurement target person having any social relationship is a "social behavior receiver", the relationship between the respective measurement target persons in the social relationship management table 312 can be defined by registering the relationship between them by the measurement target person him/herself in advance. For instance, in the example of FIG. 6, as regards a relationship registration number "R0001", a relationship with a measurement target person "U00002" who is the "social behavior receiver" seen from a measurement target person "U00001" who is the "social behavior originator" is registered as "RE (parent)".

In addition, generally, as the social relationships, it can be said that a relative has a stronger relationship than an unrelated person and, even among unrelated persons, a friend has a stronger relationship than a simple acquaintance. To reflect these strength levels between the relationships to the sociality measurement, such a relationship weight table as shown in FIG. 7 may be stored as an attached table of the social relationship management table 312.

FIG. 8 is a view showing an example of the behavior pattern management table 313. In the behavior pattern management table 313, a behavior pattern identification number is assigned to each behavior pattern, and various behavior patterns are managed by using the behavior pattern identification numbers. Here, the behavior pattern is information classified in relation to at least one of behavior and emotion of the measurement target person. It is to be noted that the behavior pattern management table 313 is provided for each account which is used for acquisition of the social behavior information. FIG. 8 shows the behavior pattern management table 313 when a GPS is used as an account.

On the other hand, FIG. 9 shows an example of the behavior pattern management table 313 when text data of, e.g., an email is used as an account. The example of using the behavior pattern management table 313 will be described later in "Modification 2" in detail.

FIG. 11 is a view showing an example of the sociality item management table 314. The sociality item management table 314 is a table in which a sociality item to be measured, contents thereof, a relationship to which reference is made at the time of measuring each sociality item, and a behavior pattern are managed in association with each other. It is to be noted that, as the sociality items to be measured, various references can be adopted. In this embodiment, an example of using the sociality QOL indexes shown in FIG. 10 will be described.

The display circuitry 32 is a display, and the input circuitry 33 is an input device (an input interface circuit) such as a touch panel, a keyboard, a numerical keypad, or a mouse. The display circuitry 32 is a display, and displays a GUI for various kinds of operations, the later-described sociality measurement report, and the like as required. The input circuitry 33 is realized by, e.g., a mouse, a numerical keypad, a keyboard, a touch pad through which an instruction is input when an operation surface is touched, and the like. The input circuitry 33 accepts various kinds of instructions from the measurement target person. The input circuitry 33 is connected to the control circuitry 30 through, e.g., the bus, converts an operation instruction input from the measurement target person into an electrical signal, and outputs the electrical signal to the control circuitry 30. It is to be noted that, in this embodiment, the input circuitry 33 is not restricted only to input circuitry including physical operation components, e.g., the mouse or the numerical keypad. For example, an electrical signal processing circuit which receives an electrical signal corresponding to an operation instruction input from an external input device provided separately from the external server 3 and outputs this electrical signal to the control circuitry 30 is also included in the example of the input circuitry 33.

The network communication circuitry 34 is an interface which transmits or receives data to or from the information processing terminal 2 owned by each measurement target person through the network N, and realized by, e.g., a communication port, a router, or the like. In particular, in processing which follows the later-described sociality measurement function, the sociality behavior information generated by the information processing terminal 2 is received through the network N, and the sociality measurement report generated by the sociality measurement report generation function 303 is transmitted to the information processing terminal 2 through the network N.

The output circuitry 35 outputs the sociality measurement report generated by the sociality measurement report generation function 303 in a predetermined mode (e.g., printout) as required.

(Sociality Measurement Function)

The sociality measurement function realized by this medical information system 1 will now be described. This function is configured to collect the social behavior information of the measurement target person at any time by using the information processing terminal 2 owned by the measurement target person registered in this medical information system 1, quantitatively measure the sociality of the measurement target person based on the collected information, and support the sociality QOL evaluation.

Processing which follows this sociality measurement function (sociality measurement processing) can be roughly classified into (1) a social behavior acquisition/social behavior information generation phase in the information processing terminal 2 owned by the measurement target person, (2) a social behavior information analysis/sociality measurement phase in the external server 3 installed on the hospital side, and (3) a sociality measurement report generation/output phase. Contents of each phase will be described below in detail.

(1) Social Behavior Acquisition/Social Behavior Information Generation Phase

Figure 12:
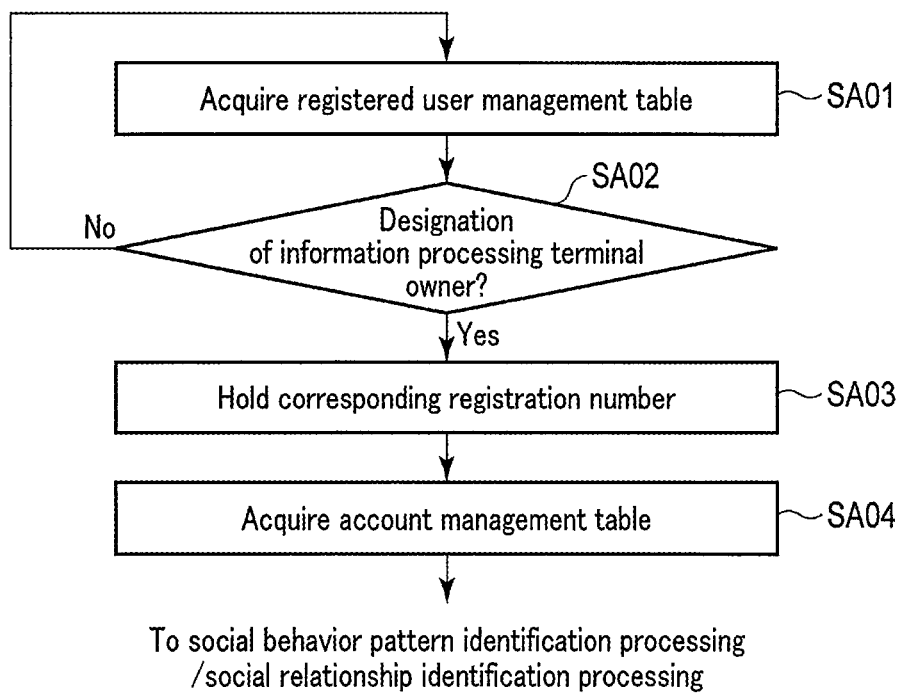
FIG. 12 is a flowchart showing a flow of processing to start automatic acquisition of social behavior information and automatic transmission of the same to an external server 3 in the information processing terminal 2.

FIG. 12 is a flowchart showing a flow of processing in the information processing terminal 2 to start social behavior automatic acquisition, social behavior information automatic generation, and automatic transmission to the external server 3. It is to be noted that the social behavior information automatic acquisition and the automatic transmission which follow this flow may be started at arbitrary timing, but the timing is typically, e.g., timing of evaluating the QOL before and after a medical treatment under a physician's direction after determining that the measurement target person who is a measurement target performs a predetermined medical act.

As shown in FIG. 12, first, the social behavior information generation function 200 of the information processing terminal 2 acquires the registered measurement target person management table 310 (see FIG. 4) from the storage circuitry 31 in the external server 3 through the network N (a step SA01), and accepts designation of an owner (a holder) of the information processing terminal 2 in response to an input from the measurement target person (a step SA02). In this embodiment, to give a specific description, it is assumed that "Taro Tokkyo" having a registration number "U00001" is designated as a holder of the terminal 2 in FIG. 4.

The social behavior information generation function 200 holds the designated "registration number U00001: Taro Tokkyo" (a step SA03), and acquires the account management table 311 (see FIG. 5) from the storage circuitry 31 in the external server 3 through the network N (a step SA04).

The social behavior information generation function 200 acquires the social behavior information in accordance with a cycle and an account in contents of the acquired account management table 311. In a current case, as the holder of the information processing terminal 2, "registration number U00001: Taro Tokkyo" is held. Thus, according to the account management table 311 shown in FIG. 5, three account types, i.e., "phone number", "GPS", and "email address" are registered, and access schedules to the respective accounts are defined as "cycle T1", "cycle T2", and "cycle T3". To give a specific description below, in this embodiment, an example where the account type is "GPS" and hence the social behavior information is acquired with the "cycle T2" will be adopted.

Figure 13:
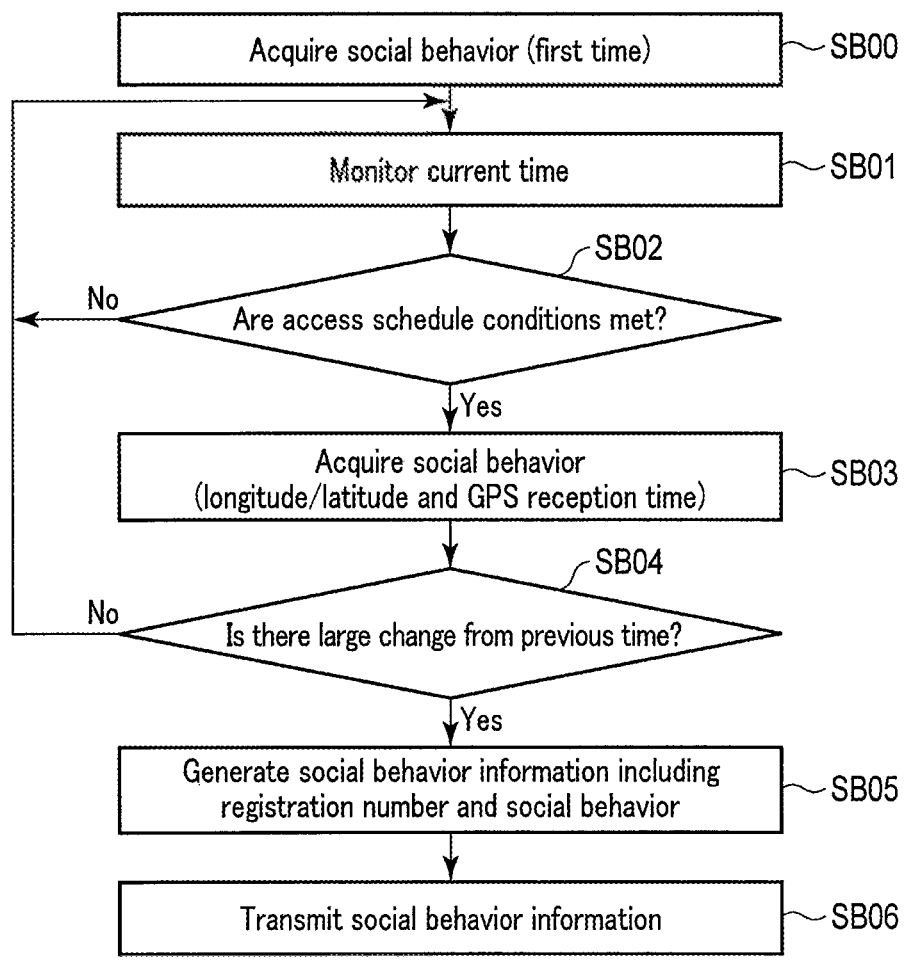
FIG. 13 is a flowchart showing a flow of social behavior automatic acquisition, social behavior information automatic generation, and automatic transmission processing to the external server 3 in the information processing terminal 2.

FIG. 13 is a flowchart showing a flow of the social behavior automatic acquisition, the social behavior information automatic generation, and the automatic transmission processing to the external server 3 in the information processing terminal 2. As shown in the drawing, the social behavior information generation function 200 controls the social behavior acquisition circuitry 25, inputs designation of a holder at the step SA02, and then acquires GPS information (i.e., current degrees of latitude and longitude of the information processing terminal 2 and a reception time) as initial social behavior (a step SB00).

Then, the social behavior information generation function 200 monitors a current time (a step SB01), and determines whether a condition of the access schedule is met (in this case, whether the cycle T2 has passed from a time at which previous social behavior was acquired) (a step SB02). Consequently, when it has been determined that the condition of the access schedule is met, the social behavior information generation function 200 controls the social behavior acquisition circuitry 25 to acquire the GPS information as the social behavior (a step SB03). On the other hand, when it has been determined that the condition of the access schedule is not met, the social behavior information generation function 200 continues monitoring the current time.

Subsequently, the social behavior information generation function 200 compares the previously acquired social behavior with the currently acquired social behavior, and determines whether a difference between them falls within a predetermined range (a step SB04). As a result of the determination, when the difference between the previously acquired social behavior and the currently acquired social behavior falls within the predetermined range (e.g., when a fluctuation in degrees of latitude and longitude falls within a predetermined range), the social behavior automatic acquisition processing described in the step SB01 to the step SB04 is repeatedly executed. On the other hand, when the previously acquired social behavior is compared with the currently acquired social behavior information and the difference between them is out of the predetermined range (e.g., a fluctuation in at least one of the degree of latitude and the degree of longitude is larger than a predetermined range), the social behavior information generation function 200 generates social behavior information including the current social behavior acquired at the step SB03 and "registration number U00001" held at the step SA03 (a step SB05). The network communication circuitry 24 transmits the generated social behavior information to the external server 3 through the network N (a step SB06).

(2) Social Relationship/Social Behavior Pattern Identification and Sociality Measurement Phase FIG. 14 is a view showing a flow of the social relationship identification processing in the external server 3. As shown in FIG. 14, the social behavior information collection function 300 collects the social behavior information transmitted from the information processing terminal 2 through the network communication circuitry 34 (a step SC01). Furthermore, the social behavior information collection function 300 collects online or offline the social behavior information of each measurement target person other than the measurement target person corresponding to the registration number "U00001" included in the collected social behavior information (a step SC02).

The social relationship/social behavior pattern identification function 301 determines whether social behavior whose difference from the social behavior (the GPS information) of the measurement target person having the registration number "U00001" collected at the step SC01 is a predetermined threshold value or less (a fluctuation in degrees of latitude and longitude is a predetermined threshold value or below) is present (i.e., whether any other measurement target person is present near the measurement target person having the registration number "U00001") in pieces of social behavior (the GPS information) included in the social behavior information of each of other measurement target persons collected at the step SC02 (a step SC03). As a result of the determination, when the social behavior whose difference is the threshold value or less is present, the social relationship/social behavior pattern identification function 301 acquires a registration number of another measurement target person corresponding to the social behavior whose difference is the threshold value or less (a step SC04-1). On the other hand, as a result of the determination, when the social behavior whose difference is the threshold value or less is not present, the social relationship/social behavior pattern identification function 301 executes processing on the assumption that "registration number: U0000 (Unknown)" has been acquired (a step SC04-2).

Next, the social relationship/social behavior pattern identification function 301 uses the registration number "U00001" of the measurement target person, a registration number of another measurement target person acquired at the step SC04-1, and the social relationship management table 312 (see FIG. 6) to determine whether a social relationship defined between these persons is present (a step SC05). As a result of the determine, when the social relationship defined between them is present, a corresponding relationship identification number is acquired by making reference to the social relationship management table 312, and a weight of this relationship is also acquired by making reference to a relationship weight management table (a step SC06-1). For example, if the registration number of another measurement target person acquired at the step SC04-1 is "U00002", a relationship identification number "RE10 (friend)" defined between these persons is acquired by making reference to the social relationship management table 312 shown in FIG. 6, and a weight "3" of the relationship identification number "RE10 (friend)" is acquired by making reference to the relationship weight management table shown in FIG. 7. On the other hand, as a result of the determination, when no social relationship defined between these persons is present or when "registration number: U0000 (Unknown)" has been acquired at the step SC04-2, the relationship identification number "RE0 (unrelated person)" is acquired (a step SC06-2).

Figure 15:
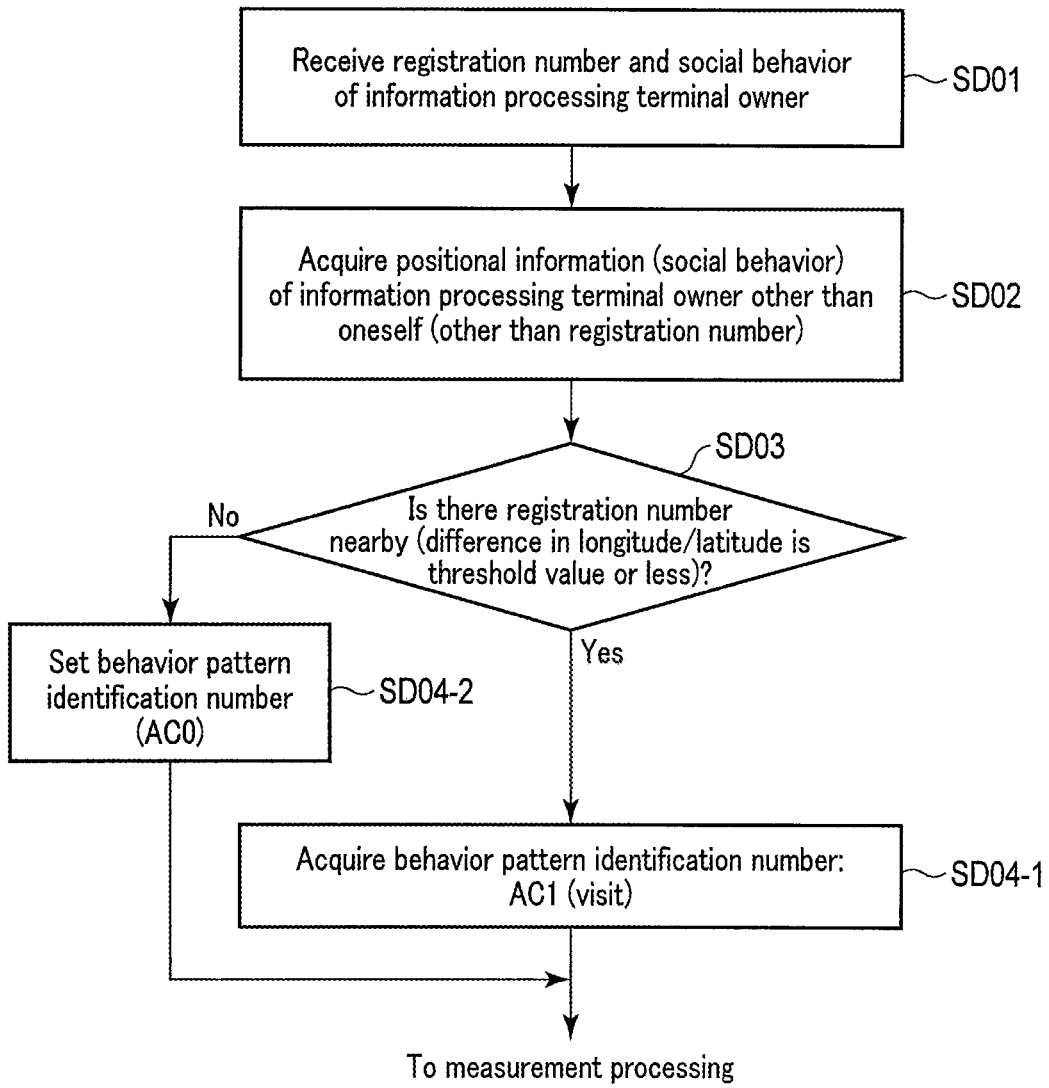
FIG. 15 is a view showing a flow of social behavior pattern identification processing in the external server 3.

FIG. 15 is a view showing a flow of the social behavior pattern identification processing in the external server 3. As shown in FIG. 15, the social behavior information collection function 300 collects the social behavior information of the measurement target person (a step SD01) and collects the social behavior (GPS information) of each of other measurement target persons (a steps SD02) as the same processing having the configuration described in the step SC01 to the step SC03 in FIG. 14.

The social relationship/social behavior pattern identification function 301 determines whether social behavior whose fluctuation in degrees of latitude and longitude is a predetermined threshold value or less is present (a step SD03). As a result of the determination, when the social behavior whose difference is the threshold value or less is present, the social relationship/social behavior pattern identification function 301 acquires a behavior pattern identification number concerning the current social behavior by making reference to the behavior pattern management table 313 stored in the storage circuitry 31 (a step SD04-1). It is to be noted that, in this embodiment, the GPS information (positional information) is used as the social behavior. In such a case, for example, a behavior pattern identification number "AC1 (visit)" corresponding to the GPS information is acquired by making reference to the behavior pattern management table 313 shown in FIG. 8. On the other hand, as a result of the determination, when the social behavior whose difference is the threshold value or less is not present, the social relationship/social behavior pattern identification function 301 executes processing on the assumption that "behavior pattern identification number: AC0 (Unknown)" has been acquired (a step SD04-2).

The social behavior information collection collected by the processing shown in FIG. 14 and FIG. 15 described above, the social relationship identification, and the social behavior pattern identification are automatically executed at predetermined timing (e.g., periodic timing such as every week or every month). The social relationship/social behavior pattern identification function 301 updates the relationship/behavior pattern management table as a history over such a predetermined period as shown in FIG. 16 for each registered measurement target person every time the relationship identification and the behavior pattern identification are completed. The relationship/behavior pattern management table is stored in the storage circuitry 31 every time it is updated, and used in the sociality measurement processing which will be described next.

Figure 17:
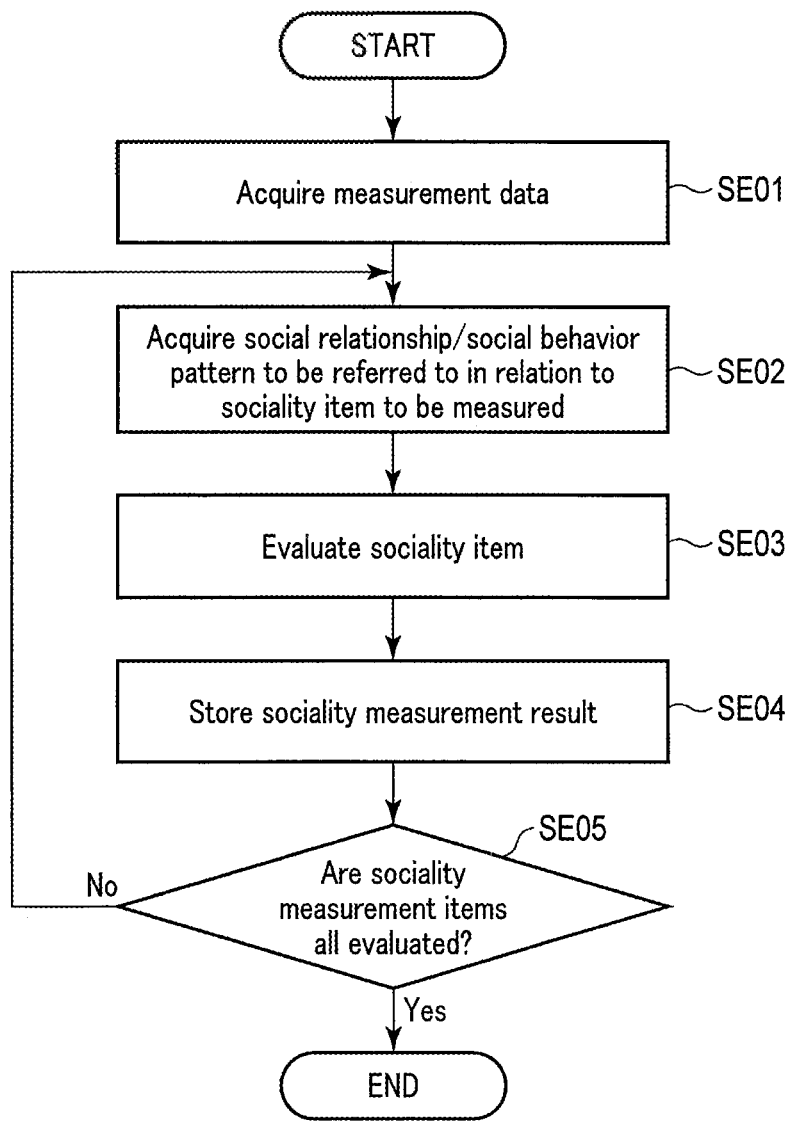
FIG. 17 is a view showing a flow of sociality measurement processing in the external server 3.

FIG. 17 is a view showing a flow of the sociality measurement processing in the external server 3. As shown in FIG. 17, the sociality measurement function 302 uses the relationship/behavior pattern management table stored in the storage circuitry 31 to extract such a relationship/behavior pattern management table as shown in FIG. 18 which belongs to a corresponding period (e.g., from Jun. 1, 2016 to Jun. 6, 2016) about the measurement target person "registration number: U00001: Taro Tokkyo" (a step SE01).

The sociality measurement function 302 designates a relationship/behavior pattern to be referred to for each preset sociality item to be measured on the basis of the sociality item management table 314 (see FIG. 11) (a step SE02), and executes evaluation of the sociality item (a step SE03). It is to be noted that, to give a specific description below, for example, "S1 (number of visits to friends is decreasing" is designated as the sociality item, and "RE10 (friend)" and "AC1 (visit)" are designated as the relationship to be referred to and the behavior pattern to be referred.

FIG. 19 is a flowchart showing a flow of processing to evaluate the sociality item "S1 (number of visits to friends is decreasing)" by a comparison with the target person's past data at the step SE03. As shown in FIG. 19, the sociality measurement function 302 acquires the relationship pattern "RE10 (friend)" and the behavior pattern "AC1 (visit)" to be referred to, which have been designated at the step SE02, from measurement data (the relationship/behavior pattern management table belonging to a corresponding period shout the measurement target person) (a step SF01), and measures the number of times (a total number) of the acquired relationship pattern and behavior pattern (a step SF02). Moreover, the sociality measurement function 302 acquires the number of times of measurement of "RE10 (friend)" and the behavior pattern "AC1 (visit)" in relation to the previous sociality item "S1 (number of visits to friends is decreasing)" (a step SE03), and determines (evaluates) a magnitude relation of the current number of times of measurement and the previous number of times of measurement (a step SF04). As a result of the determination, when the current number of times of measurement is lower than the previous number of times of measurement, the sociality measurement function 302 determines that the sociality item "S1 (number of visits to friends is decreasing)" is applicable (a step SF05-1). On the other hand, as a result of the determination, when the current number of times of measurement is higher than the previous number of times of measurement, the sociality measurement function 302 determines that the sociality item "S1 (number of visits to friends is decreasing)" is not applicable (a step SF05-2).

Again referring to FIG. 17, the sociality measurement result provided by the evaluation processing shown in FIG. 19 is stored in the storage circuitry 31 (a step SE04). Additionally, when multiple sociality items to be measured are present, the sociality measurement function 302 executes the evaluation processing shown in FIG. 19 for each item to acquire each sociality measurement result (a step SE05).

Consequently, as to each of the sociality items to be measured, such a sociality measurement result as shown in FIG. 20 can be provided over a predetermined period. The sociality measurement result can be likewise created by a predetermined classification, e.g., an individual basis, an organization basis, a monthly basis, an annual basis, or the like.

It is to be noted that in the example shown in FIG. 19, the sociality item is evaluated by comparing the current number of times of measurement with the previous number of times of measurement. However, the sociality item may be evaluated by using any other reference without being restricted to this example.

FIG. 21 is a flowchart showing a flow of processing to evaluate the sociality item "S1 (number of visits to friends is decreasing)" by a comparison with a reference value provided by the statistical processing at the step SE03 in FIG. 17. In FIG. 21, the sociality measurement function 302 acquires the relationship pattern "RE10 (friend)" and the behavior pattern "AC1 (visit)", which are to be referred to, from the measurement data like the example of FIG. 19 (a step SG01), and measures a number of times (a total number) of the acquired relationship pattern and behavior pattern (a step SG02). Further, the sociality measurement function 302 acquires measurement data concerning the sociality item "S1" of other persons which are samples from the relationship/behavior pattern management table concerning all the measurement target persons shown in FIG. 16 (a step SG03), and calculates an average value of the numbers of times of measurement of the relationship pattern "RE10 (friend)" and the behavior pattern "AC1 (visit)" which are to be referred to (a step SG04). Subsequently, the sociality measurement function 302 determines (evaluates) a magnitude relation of the current number of times of measurement (of the measurement target person) acquired at the step SG03 and an average value of the numbers of times of measurement of other persons calculated at the step SG04 (a step SG05). As a result of the determination, when the current number of times of measurement of the measurement target person is lower than the average value of the numbers of times of measurement of the other persons, the sociality measurement function 302 determines that the sociality item "S1 (number of visits to friends is decreasing)" is applicable (a step SG06-1). On the other hand, as a result of the determination, when the current number of times of measurement of the measurement target person is higher than the average value of the numbers of times of measurement of the other persons, the sociality measurement function 302 determines that the sociality item "S1 (number of visits to friends is decreasing" is not applicable (a step SG06-2).

In the example using FIG. 21, the sociality item "S1 (number of visits to friends is decreasing)" is evaluated by the comparison with the reference value provided by the statistical processing. However, any other measurement target person close to the measurement target person may be selected by using a predetermined reference, and the number of times of measurement of the relationship pattern and the behavior pattern of the other measurement target person may be determined as a reference value to evaluate the sociality item "S1 (number of visits to friends is decreasing)" without being restricted to this example. That is, even if not only information (including information subjected to the statistical processing) provided from the other measurement target persons but also information provided from any other specific measurement target person (they will be collectively referred to as "information of others") are used, the sociality item can be evaluated.

When the above-described reference is used, the sociality measurement item of the measurement target person can be likewise preferably evaluated. It is to be noted that, in the determination of the step SG05, besides the magnitude relation of the current number of times of measurement and the average value of the numbers of times of measurement of others, the numbers of times of measurement of others may be used to calculate a standard deviation, and the determination may be made on the basis of "whether the current number of times of measurement belongs to a range of the average value of the numbers of times of measurement of others±the standard deviation". Further, any other statistical value (e.g., a median) or the like may be adopted without being restricted to the average value.

(3) Sociality Measurement Report Generation/Output Phase

The sociality measurement generation function 303 generates a sociality measurement report of the measurement target person on the basis of the obtained sociality measurement result, and outputs it in a predetermined mode.

FIG. 22A shows an example of the generated sociality measurement report. As shown in the drawing, in the sociality measurement report, as regards the sociality QOL of the measurement target person in a target period, presence/absence of applicability and its detail are shown for each sociality measurement item, and comprehensive evaluation is measured as a quantitative value using a "total score (e.g., an average value considering a weight coefficient of the sociality measurement item)". Furthermore, as feedback of a sociality measurement result to the measurement target person, the sociality measurement report does not have to be necessarily provided, and attention may be called by an alert or the like on the basis of, e.g., a comparison result of a score of the sociality measurement item or a total score with a preset threshold value.

FIG. 22B shows an example of a sociality measurement report generated when the statistical reference shown in FIG. 21 is used. As shown in the drawing, besides information concerning the measurement target person, the number of corresponding persons in the entire measurement target persons who use the system is shown for each sociality measurement item. Such statistical information may be represented by using a graph or the like.

Moreover, in the foregoing embodiment, as its example, the GPS information is used as the social behavior, a social relationship between the measurement target person and any other person is identified by using the social behavior and the social relationship management table shown in FIG. 6, and the behavior pattern of the measurement target person is identified by using the collected social behavior and the behavior pattern table shown in FIG. 8.

However, the medical information system according to this embodiment can adopt, e.g., configurations described in the following Modification 1 to Modification 5 without being restricted to this example. The configurations described in Modification 1 to Modification 5 collect information concerning communication performed by the measurement target person to any other person as social behavior information, and analyze the information concerning the communication performed by the measurement target person to the other person to identify asocial relationship between the measurement target person and the other person and a behavior pattern of the measurement target person. It is to be noted that the above-described configuration can be arbitrarily combined with the respective configurations described in the following Modification 1 to Modification 5 as a matter of course.

(Modification 1)

A medical information system according to Modification 1 uses positional information provided by using proximity communication (e.g., Wi-fi (a registered trademark), Blue-tooth (a registered trademark), or the like) as social behavior. In an information processing terminal 2 according to this Modification 1, social behavior acquisition circuitry 25 shown in FIG. 2 comprises a structure as a proximity communication circuitry (a Wi-fi (a registered trademark) router, a Blue-tooth (a registered trademark) communication terminal, or the like) which performs the proximity communication. It is to be noted that, in this Modification 1 and later-described Modifications 2, 3, and 4, (3) processing concerning a sociality measurement report generation/output phase is substantially the same as the above-described contents. A description will now be given as to (1) a social behavior acquisition/social behavior information generation phase in the information processing terminal 2 owned by a measurement target person and (2) a social relationship/social behavior pattern identification and sociality measurement phase in an external server 3 installed on a hospital side.

FIG. 23 is a flowchart showing a flow of social behavior automatic acquisition by the proximity communication, social behavior information automatic generation, and automatic transmission processing in the information processing terminal 2. As shown in the drawing, a social behavior information generation function 200 controls the social behavior acquisition circuitry 25 to acquire proximity communication information (i.e., a terminal identification number (account information) of the other end which has performed the proximity communication with the information processing thermal 2, and a time at which the proximity communication was performed) as initial social behavior (a step SB10).

Then, the social behavior information generation function 200 monitors a current time (a step SB11), and determines whether a set time has elapsed from a time at which previous social behavior was acquired (a step SB12). Consequently, when the elapse of the set time has been determined, proximity communication information as new social behavior is acquired (a step SB14) while maintaining the previous social behavior acquisition time (a step SB13). On the other hand, when no elapse of the set time from the time at which the previous social behavior was acquired has been determined, the social behavior information generation function 200 continues monitoring of the current time.

Subsequently, the social behavior information generation function 200 compares the previously acquired social behavior with currently acquired social behavior, and determines whether the social behavior has been updated from the previous time (whether a terminal identification number of the other end which performed the proximity communication with the information processing terminal 2 has been changed) (a step SB15). As a result of the determination, when the social behavior has not been updated from the previous time, the social behavior automatic acquisition processing described in the step SB11 to the step SB15 is repeatedly executed. On the other hand, as a result of the determination, when the social behavior has been updated from the previous time, the social behavior information generation function 200 generates social behavior information which includes the current social behavior acquired at the step SB14 and "registration number U00001" held at the step SA03 (a step SB16). Network communication circuitry 24 transmits the generated social behavior information to an external server 3 through a network N (a step SB17).

Figure 24:
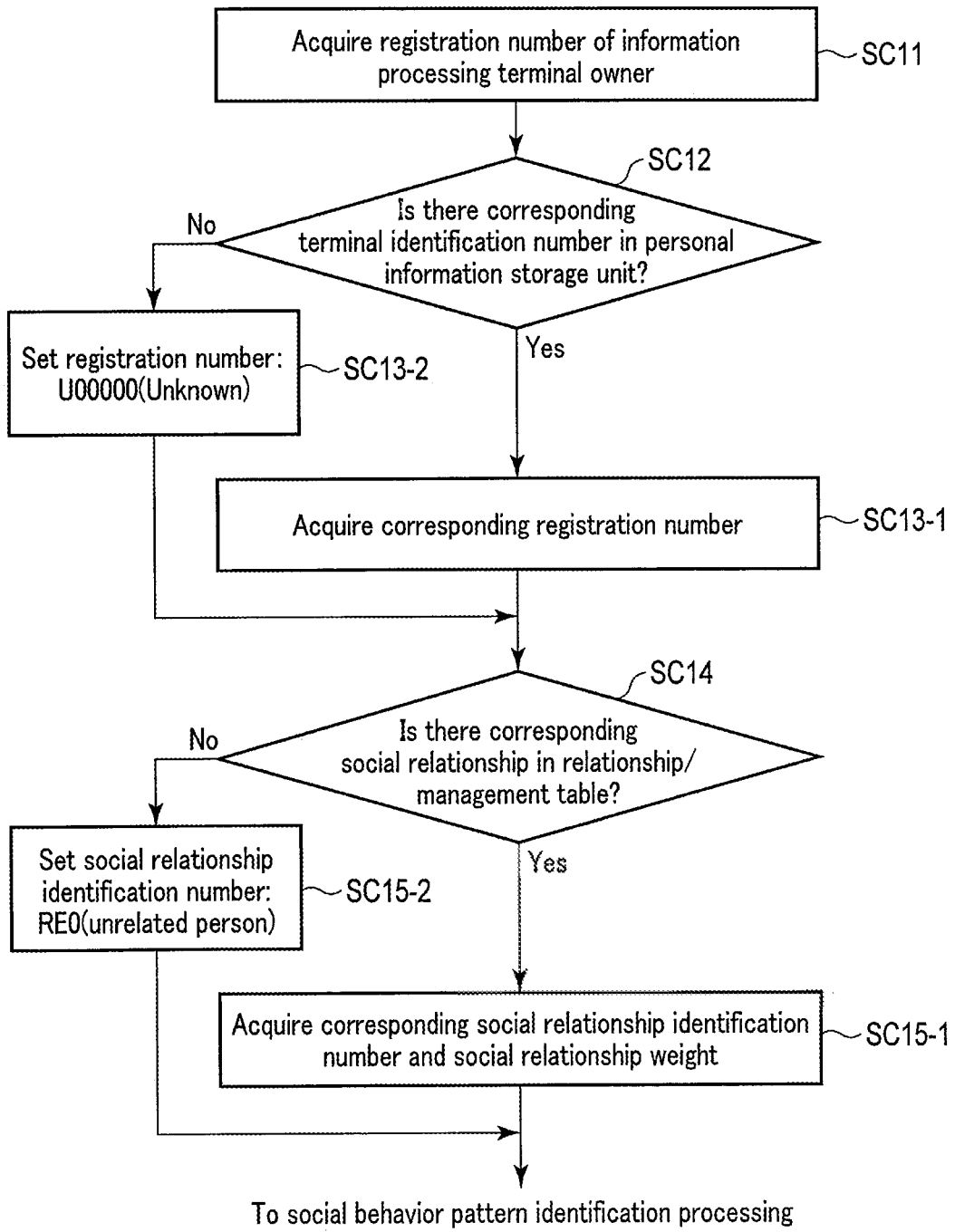
FIG. 24 is a view showing a flow of social relationship identification processing according to Modification 1.

FIG. 24 is a view showing a flow of social relationship identification processing according to this Modification 1. As shown in FIG. 24, a social behavior information collection function 300 collects social behavior information (in this case, the terminal identification number of the other end which has performed the proximity communication with the information processing terminal 2, a time at which the proximity communication was performed, and "registration number U00001" held at the step SA03) transmitted from the information processing terminal 2 through network communication circuitry 34 (a step SC11).

Further, a social relationship/social behavior pattern identification function 301 determines whether the terminal identification number of the other end included in the collected social behavior information is present in an account management table 311 (a step SC12). As a result of the determination, when the terminal identification number of the other end is present, the social relationship/social behavior pattern identification function 301 acquires a registration number corresponding to the terminal identification number of the other end from the account management table 311 (a step SC13-1). On the other hand, as a result of the determination, when the terminal identification number of the other end is not present, the social relationship/social behavior pattern identification function 301 executes processing on the assumption that "registration number: U0000 (Unknown)" has been acquired (a step SC13-2).

Next, the social relationship/social behavior pattern identification function 301 uses the registration number "U00001" of the measurement target person and the registration number of the other measurement target person acquired at the step SC13-1 or the step SC13-2 to determine whether a defined social relationship is present between these persons (a step SC14). As a result of the determination, when the defined social relationship is present between these persons, a corresponding relationship identification number is acquired by making reference to a social relationship management table 312, and a weight of this relationship is acquired by making reference to a relationship weight management table (a step SC15-1). On the other hand, as a result of the determination, when the defined social relationship is not present between these persons, or when "registration number: U0000 (Unknown)" has been acquired at the step SC13-2, a relationship identification number "RE0 (unrelated person)" is acquired (a step SC15-2). FIG. 25 is a view showing a flow of social behavior pattern identification processing according to this Modification 1. As shown in FIG. 25, the social relationship/social behavior pattern identification function 301 acquires a time at which the proximity communication was performed included in the social behavior information (a step SD11), and determines whether the terminal identification number of the other end included in the collected social behavior information is present like the step SC12 (a step SD12). As a result of the determination, when the terminal identification number of the other end is present, the social relationship/social behavior pattern identification function 301 acquires a behavior pattern identification number "AC1 (visit)" corresponding to the current social behavior from the behavior pattern management table 313 (a step SD13-1). On the other hand, as a result of the determination, when the terminal identification number of the other end is not present, the social relationship/social behavior pattern identification function 301 executes processing on the assumption that "behavior pattern identification number: AC0 (Unknown)" has been acquired (a step SD13-2).

(Modification 2)

A medical information system according to Modification 2 uses communication with the other person through an email as social behavior. In an information processing terminal according to this Modification 2, social behavior acquisition circuitry 25 shown in FIG. 2 is constituted as email communication circuitry which transmits or receives emails, and can be integrated with network communication circuitry 24.

Figure 26:
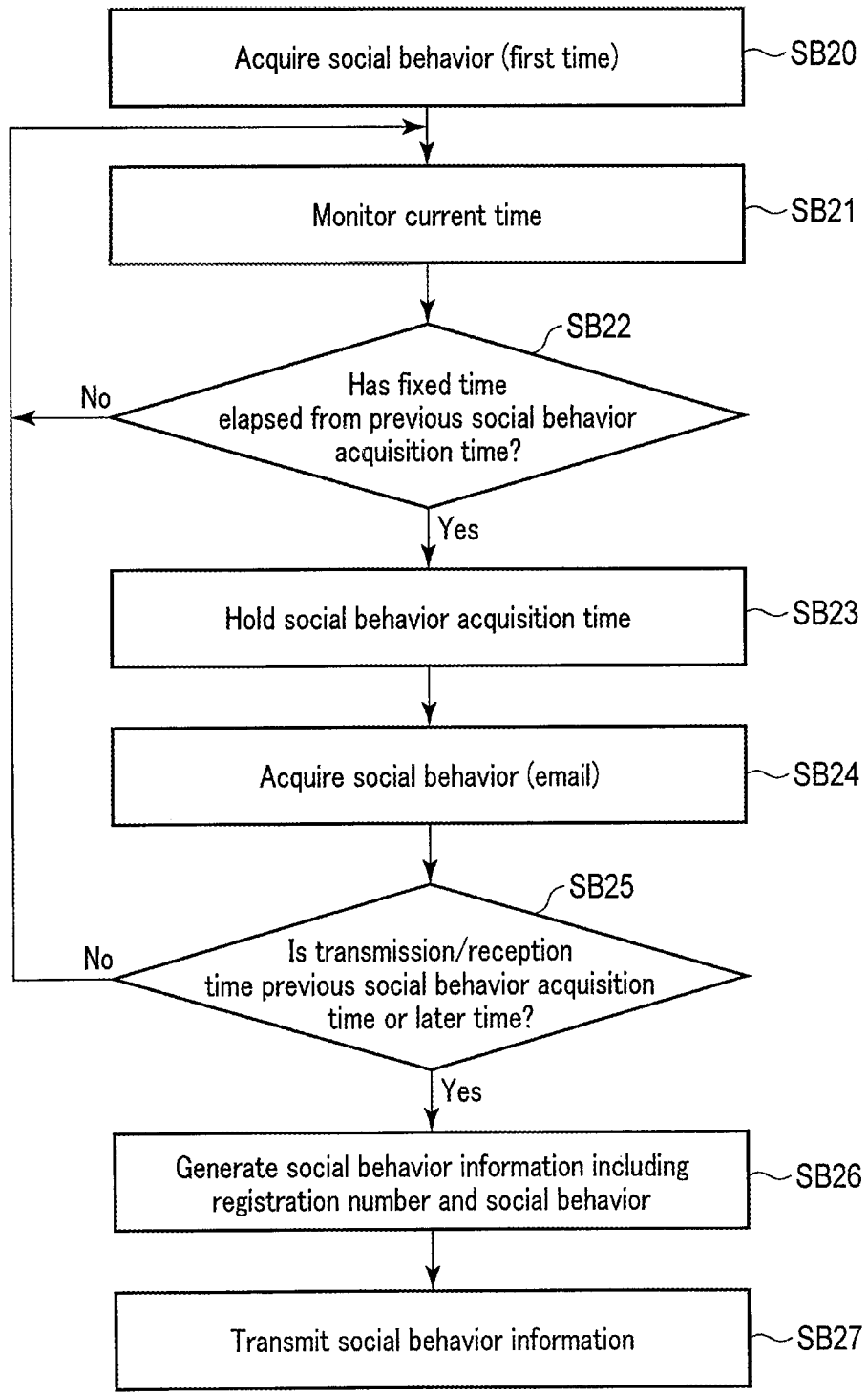
FIG. 26 is a flowchart showing a flow of social behavior automatic acquisition, social behavior information automatic generation, and automatic transmission processing according to Modification 1.

FIG. 26 is a flowchart showing a flow of social behavior automatic acquisition using email communication, social behavior information automatic generation, and automatic transmission processing in the information processing terminal 2. As shown in the drawing, a social behavior information generation function 200 controls the social behavior acquisition circuitry 25 and acquires email information (i.e., emails transmitted or received during a fixed period in the past from the present, a destination of each email or account information of a transmission source, and a transmission or reception time of each email) as initial social behavior (a step SB20).

Then, the social behavior information generation function 200 monitors a current time (a step SB21), and determines whether a set time has elapsed from a time at which previous social behavior was acquired (a step SB22). As a result, when the elapse of the set time has been determined, the email information as social behavior is freshly acquired (a step SB24) while maintaining the previous social behavior acquisition time (a step SB23). On the other hand, when no elapse of the set time from the time at which the previous social behavior was acquired has been determined, the social behavior information generation function 200 continues monitoring the current time.

Subsequently, the social behavior information generation function 200 determines whether a transmission/reception time of each email included in the currently acquired social behavior is the acquisition time of the previously acquired social behavior or a later time (a step SB25). As a result of the determination, when the transmission/reception time of each email is not the acquisition time of the previously acquired social behavior or a later time, the social behavior automatic acquisition processing described in the step SB21 to the step SB25 is repeatedly executed. On the other hand, as a result of the determination, when the transmission/reception time of each email is the acquisition time of the previously acquired social behavior or a later time, the social behavior information generation function 200 generates social behavior information including the current social behavior acquired at the step SB24 and "registration number U00001" held at the step SA03 (a step SB26). The network communication circuitry 24 transmits the generated social behavior information to an external server 3 through a network N (a step SB27). It is to be noted that email software (a mailer) of the information processing terminal 2 may automatically detect transmission/reception timing of each email, and the generated social behavior information may be automatically transmitted to the external server 3 through the network N.

FIG. 27 is a view showing a flow of social relationship identification processing according to this Modification 2. As shown in FIG. 27, the social relationship/social behavior pattern identification function 301 determines whether transmission source account information of each email included in the social behavior information is present in an account management table 311 (a step SC21). As a result of the determination, when the account information is present in the account management table 311, a registration number corresponding to the present account information is acquired (a step SC22-1). On the other hand, as a result of the determination, when the account information is not present in the account management table 311, the social relationship/social behavior pattern identification function 301 executes processing on the assumption that "registration number: U0000 (Unknown)" has been acquired (a step SC22-2).

Then, the social relationship/social behavior pattern identification function 301 determines whether account information of each email receiver included in the social behavior information is present in the account management table 311 (a step SC23). As a result of the determination, when the account information is present in the account management table 311, a registration number corresponding to the present account information is acquired (a step SC24-1). On the other hand, as a result of the determination, when the account information is not present in the account management table 311, the social relationship/social behavior pattern identification function 301 executes processing on the assumption that "registration number: U0000 (Unknown)" has been acquired (a step SC24-2).

Then, the social relationship/social behavior pattern identification function 301 uses the registration number acquired at the step SC22-1, the registration number acquired at the step SC24-1, and the social relationship management table 312 (see FIG. 6) to determine whether a defined social relationship is present between two sides (a step SC25). As a result of the determination, when the defined social relationship is present between the two sides, a corresponding relationship identification number is acquired by making reference to a social relationship management table 312, and a weight of this relationship is acquired by making reference to the relationship weight management table (a step SC26-1). On the other hand, as a result of the determination, when the defined social relationship is not present between the two sides, or when "registration number: U0000 (Unknown)" has been acquired at the step SC22-2 or the step SC24-2, a relationship identification number "RE0 (unrelated'person)" is acquired (a step SC26-2).

Figure 28:
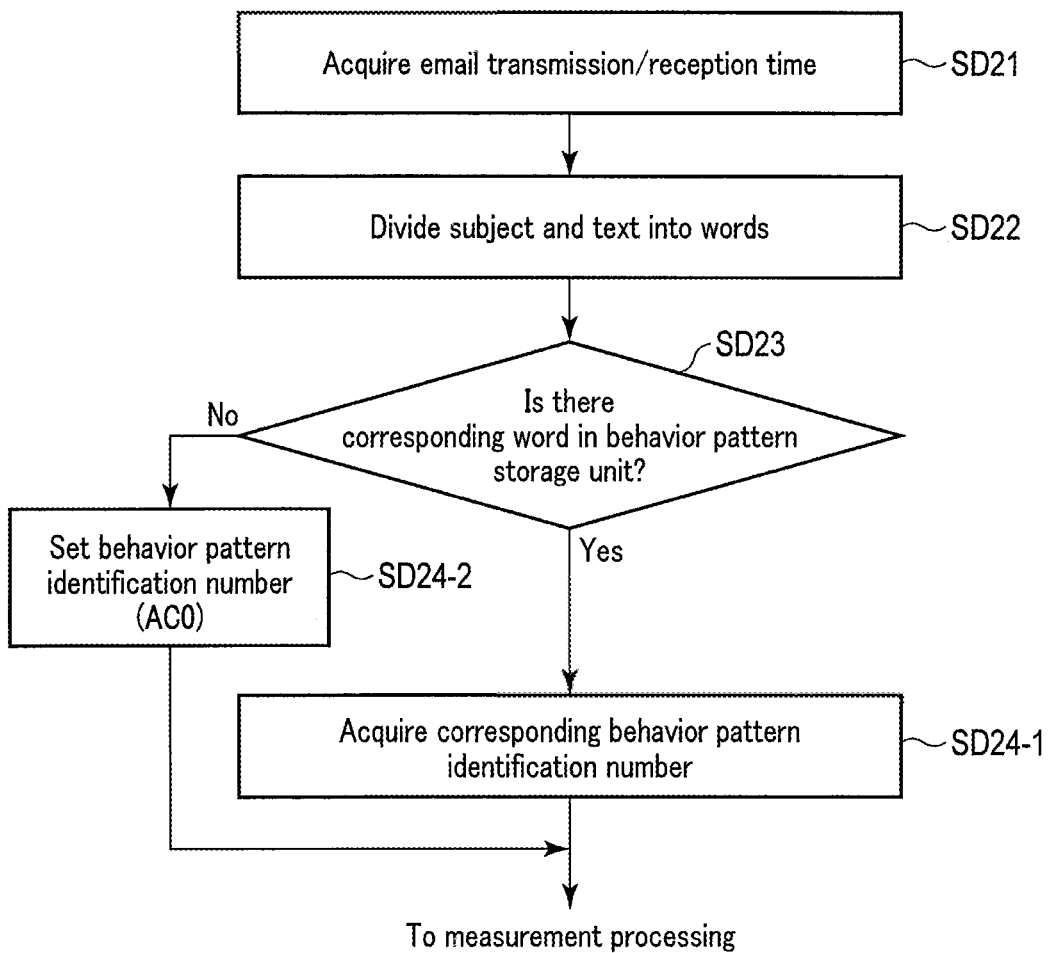
FIG. 28 is a view showing a flow of social behavior pattern identification processing according to Modification 2.

FIG. 28 is a view showing a flow of the social behavior pattern identification processing according to this Modification 2. As shown in the drawing, the social relationship/social behavior pattern identification function 301 acquires each email transmission/reception time included in the social behavior information (a step SD21), and divides a subject and a text of each email included in the social behavior information into words (a step SD22). For example, in a case where an email included in the social behavior information has a subject "are you free tomorrow?" and a text "shall we go to a park tomorrow?" and its response email has a subject "Re: are you free tomorrow?" and a text "I played too much this week and got tired", the social relationship/social behavior pattern identification function 301 divides the subject and the text of each email like "are/you/free/tomorrow/?/shall/we/go/to/a/park/tomorrow/?" and "Re:are/you/free/tomorrow/?/I/played/too/much/this/week/and/got/tired/".

The social relationship/social behavior pattern identification function 301 makes reference to, e.g., a behavior pattern management table 313 shown in FIG. 9 to determine whether each divided word is present in this table (a step SD23). At this time, it may determine whether a word which is completely the same as a word registered in the behavior pattern management table 313 is present, or it may determine whether a similar word (e.g., a specific number of letters or more matches) is present. As a result of the determination, when any one of the divided words is present, the social relationship/social behavior pattern identification function 301 acquires a behavior pattern identification number corresponding to the current social behavior from the behavior pattern management table 313 (a step SD24-1). It is to be noted that two or more words have been determined to be present in the behavior pattern management table 313 (e.g., when two words "played" and "tired" are present like the above example), individual behavior pattern identification numbers "AC4" and "AC5" are acquired. On the other hand, as a result of the determination, when the divided words are not present at all, the social relationship/social behavior pattern identification function 301 executes processing on the assumption that "behavior pattern identification number: AC0 (Unknown)" has been acquired (a step SD24-2).

(Modification 3)

A medical information system according to Modification 3 uses communication with other persons through a telephone as social behavior. Thus, in an information processing terminal 2 according to this Modification 3, social behavior acquisition circuitry 25 shown in FIG. 2 is constituted as telephone communication circuitry to realize the communication using a telephone.

Figure 29:
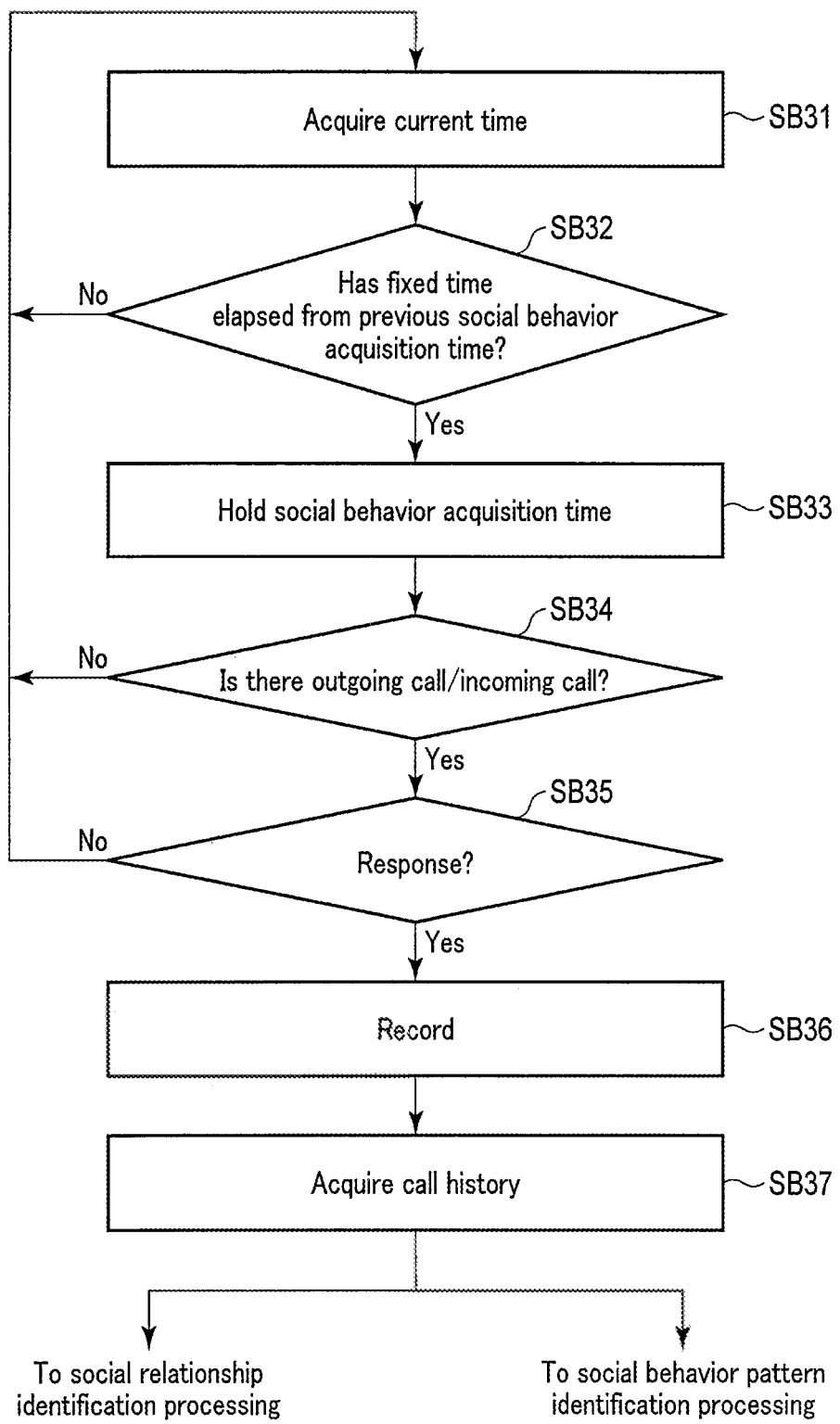
FIG. 29 is a flowchart showing a flow of social behavior automatic acquisition, social behavior information automatic generation, and automatic transmission processing according to Modification 2.

FIG. 29 is a flowchart showing a flow of social behavior automatic acquisition using communication through a telephone, social behavior information automatic generation, and automatic transmission processing in the information processing terminal 2. As shown in the drawing, a social behavior information generation function 200 monitors a current time (a step SB31), and determines whether a set time has elapsed from a time at which previous social behavior was acquired (a step SB32). As a result, when the elapse of the set time has been determined, whether a new outgoing call history/incoming call history of a telephone as social behavior is present (a step SB34) while maintaining the previous social behavior acquisition time (a step SB33). As a result of the determination, when the new outgoing call history/incoming call history of the telephone is present, whether there was a response to each outgoing call history and each incoming call history is determined (a step SB35). When the response has been determined to be present at the step SB35, the social behavior information generation function 200 acquires recorded sound concerning a telephone call to which the response was given (a step SB36), and acquires a call history (a step SB37). This recorded sound and the call history are stored and managed as social behavior information. On the other hand, it has been determined that a new outgoing call history/incoming call history of the telephone is not present at the step SB34, or when it has been determined that there was no response at the step SB35, the social behavior information generation function 200 continues monitoring the current time.

Social relationship identification processing according to this Modification 3 is substantially the same as a flow of the processing shown in FIG. 27. That is, when "address of email sender" and "address of email receiver" in FIG. 27 are processed as "phone number of caller" and "phone number of call receiver" in the same manner respectively, relationship identification according to this Modification 3 can be realized.

Figure 30:
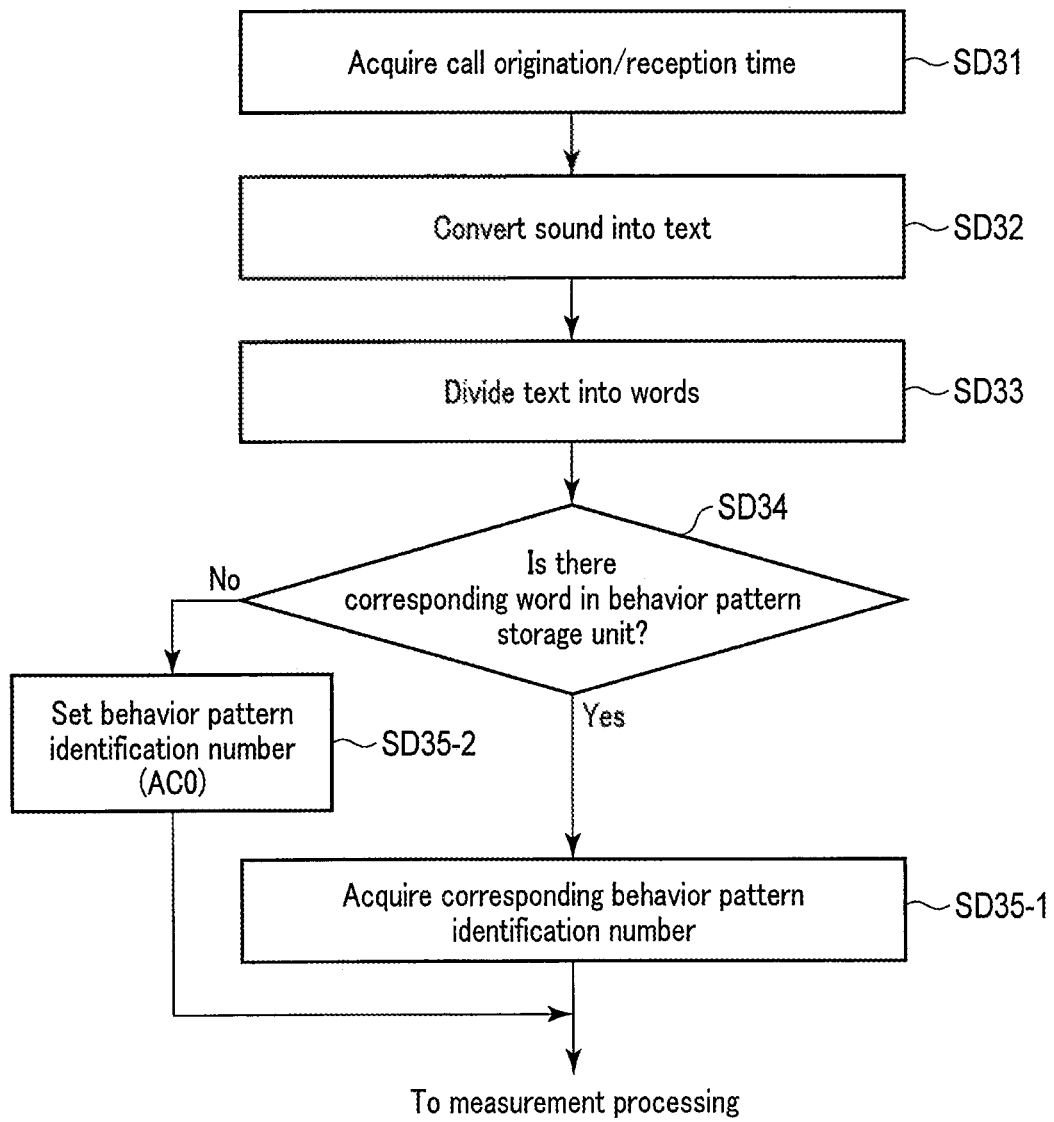
FIG. 30 is a view showing a flow of social behavior pattern identification processing according to Modification 3.

FIG. 30 is a view showing a flow of social behavior pattern identification processing according to this Modification 3. As shown in FIG. 30, a social relationship/social behavior pattern identification function 301 acquires a call origination/reception time (a step SD31), converts the recorded sound acquired at the step SB36 into a text (a step SD32), and divides the text into words (a step SD33). For example, when recorded sound "I have continuous overtime lately and cannot sleep well" is converted into a text, the social relationship/social behavior pattern identification function 301 specifically divides the text like "I/have/continuous/overtime/lately/and/cannot/sleep/well".

The social relationship/social behavior pattern identification function 301 makes reference to, e.g., behavior pattern management table 313 shown in FIG. 9 to determine whether each divided word is present in this table (a step SD34). At this time, like Modification 2, perfect matching may be adopted in the determination, or similarity may be adopted in the determination. As a result of the determination, when any divided word is present, the social relationship/social behavior pattern identification function 301 acquires a behavior pattern identification number corresponding to the current social behavior from the behavior pattern management table 313 (a step SD35-1). It is to be noted that the social relationship/social behavior pattern identification function 301 may acquire sound volume of sound data, recognize "voice becomes loud" if the sound volume is equal to or higher than a given threshold value, and identify a further detailed behavior pattern as "yell" on the basis of presence of a word representing a feeling of anger and the recognition "voice becomes loud". On the other hand, as a result of the determination, when the divided words are not present at all, the social relationship/social behavior pattern recognition function 301 executes processing on the assumption that "behavior pattern identification number: AC0 (Unknown)" has been acquired (a step SD35-2).

Figure 31:
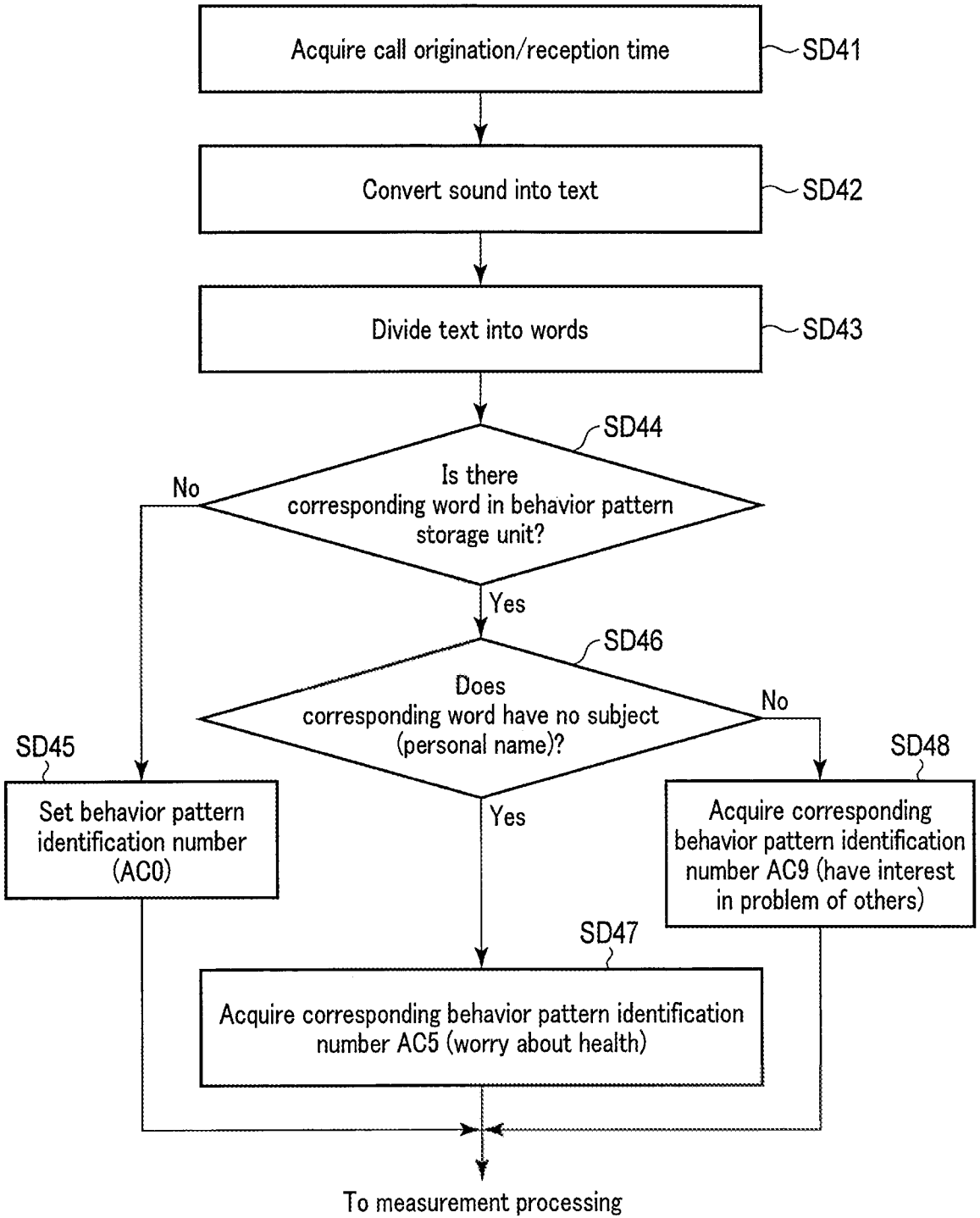
FIG. 31 is a view showing another example (including personal name determination in a text) of behavior pattern identification according to Modification 3.

FIG. 31 is a view showing another example (including a determination of a personal name in a text) of the behavior pattern identification according to this Modification 3. As shown in FIG. 31, the social relationship/social behavior pattern identification function 301 executes the same processing as that of the steps SD31 to SD34 in FIG. 30 at steps SE31 to SE34, and then determines whether a subject (a personal name) is present in words provided by dividing a text (a step SD36). At this time, perfect matching may be adopted in the determination, or similarity may be adopted in the determination. For example, when a text divided into words is "OO/said/he/had/continuous/overtime/lately/and/could/not/sleep/well", a social behavior information collection function 300 determines the personal name "OO" is present in the words provided by dividing the text.

As a result of the determination, when the personal name is present among any divided words, the social relationship/social behavior pattern identification function 301 acquires "AC9 (have interest in problem of others)" as a behavior pattern identification number corresponding to the current social behavior (a step SD37-1) from the behavior pattern management table 313. On the other hand, as a result of the determination, when the personal. name is not present among the divided words, the social relationship/social behavior pattern identification function 301 acquires "AC5 (worry about health)" as the behavior pattern identification number corresponding to the current social behavior as a result of comparing the words other than the personal name with the behavior pattern management table 313 (a step SD37-2).

(Modification 4)

The medical information system according to Modification 1 uses communication using an SNS with other persons as social behavior. Thus, in the information processing terminal 2 according to this Modification 2, social behavior acquisition circuitry 25 shown in FIG. 2 is constituted as SNS communication circuitry to realize SNS communication and can be integrated with network communication circuitry 24.

Figure 32:
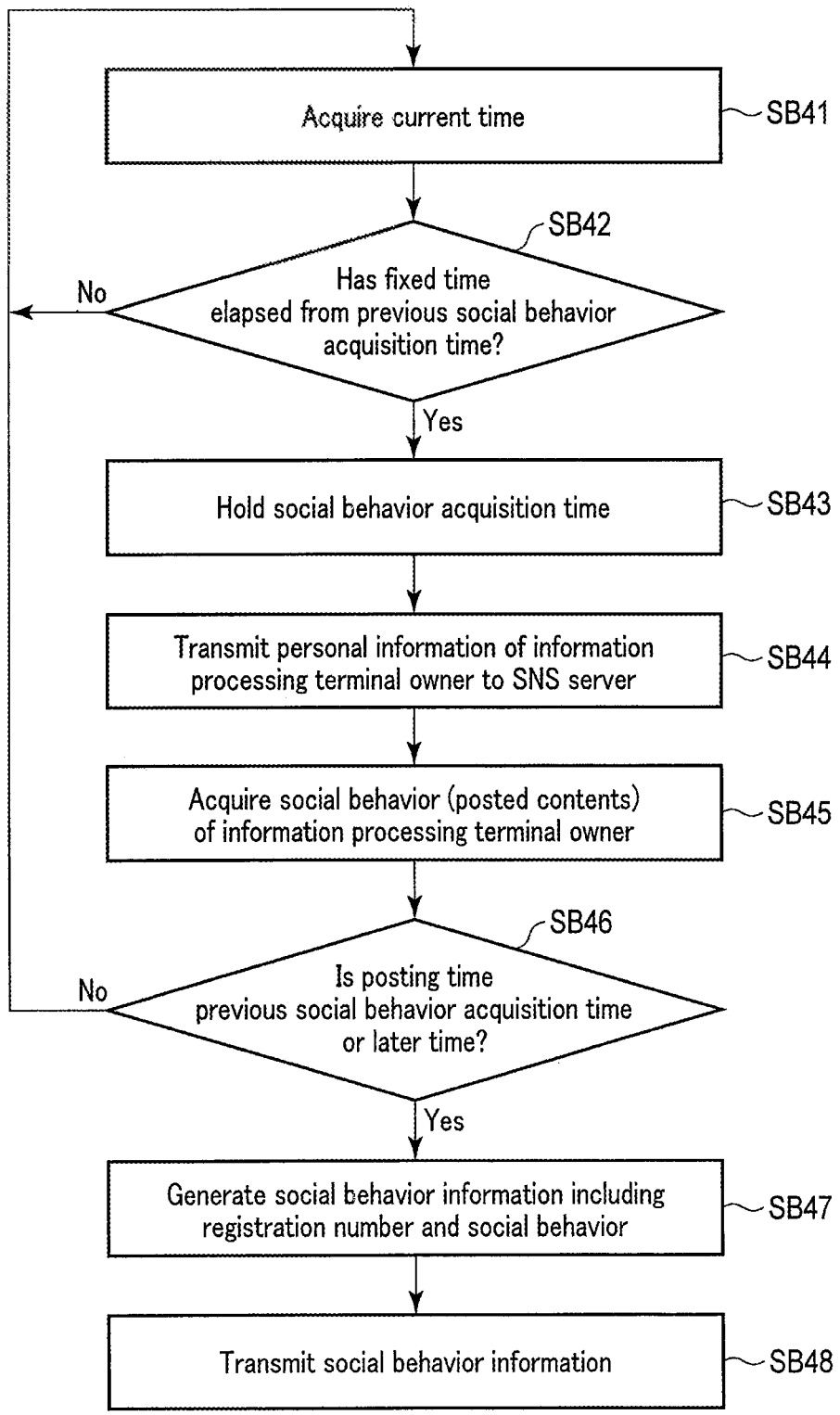
FIG. 32 is a flowchart showing a flow of social behavior automatic acquisition, social behavior information automatic generation, and automatic transmission processing according to Modification 3.

FIG. 32 is a flowchart showing a flow of social behavior automatic acquisition using SNS communication, social behavior information automatic generation, and automatic transmission processing in the information processing terminal 2. As shown in the drawing, a social behavior information generation function 200 monitors a current time (a step SB41), and determines whether a set time has elapsed from a time at which previous social behavior was acquired (a step SB42). As a result, when the elapse of the set time has been determined, personal information to identify a holder (i.e., a measurement target person) of the information processing terminal 2 is transmitted to an SNS server (a step SB44) while maintaining the previous social behavior acquisition time (a step SB43), and holder social behavior (i.e., posted contents) of the information processing terminal 2 is acquired from the SNS server (a step SB45). On the other hand, when no elapse of the set time from the time at which the previous social behavior was acquired has been determined, the social behavior information generation function 200 continues monitoring of the current time.

Subsequently, the social behavior information generation function 200 determines whether a posting time of the posted contents included in the currently acquired social behavior is the acquisition time of the previously acquired social behavior or a later time (a step SB46). As a result of the determination, when the currently acquired posting time is not the acquisition time of the previously acquired social behavior or a later time, the social behavior automatic acquisition processing described in the step SB41 to the step SB46 is repeatedly executed. On the other hand, as a result of the determination, when the currently acquired posting time is the acquisition time of the previously acquired social behavior or a later time, the social behavior information generation function 200 generates social behavior information including the current social behavior acquired at the step SB45 and "registration number U0001" held at the step SA03 (a step SB47). The network communication circuitry 24 transmits the generated social behavior information to an external server 3 through a network N (a step SB48).

Figure 33:
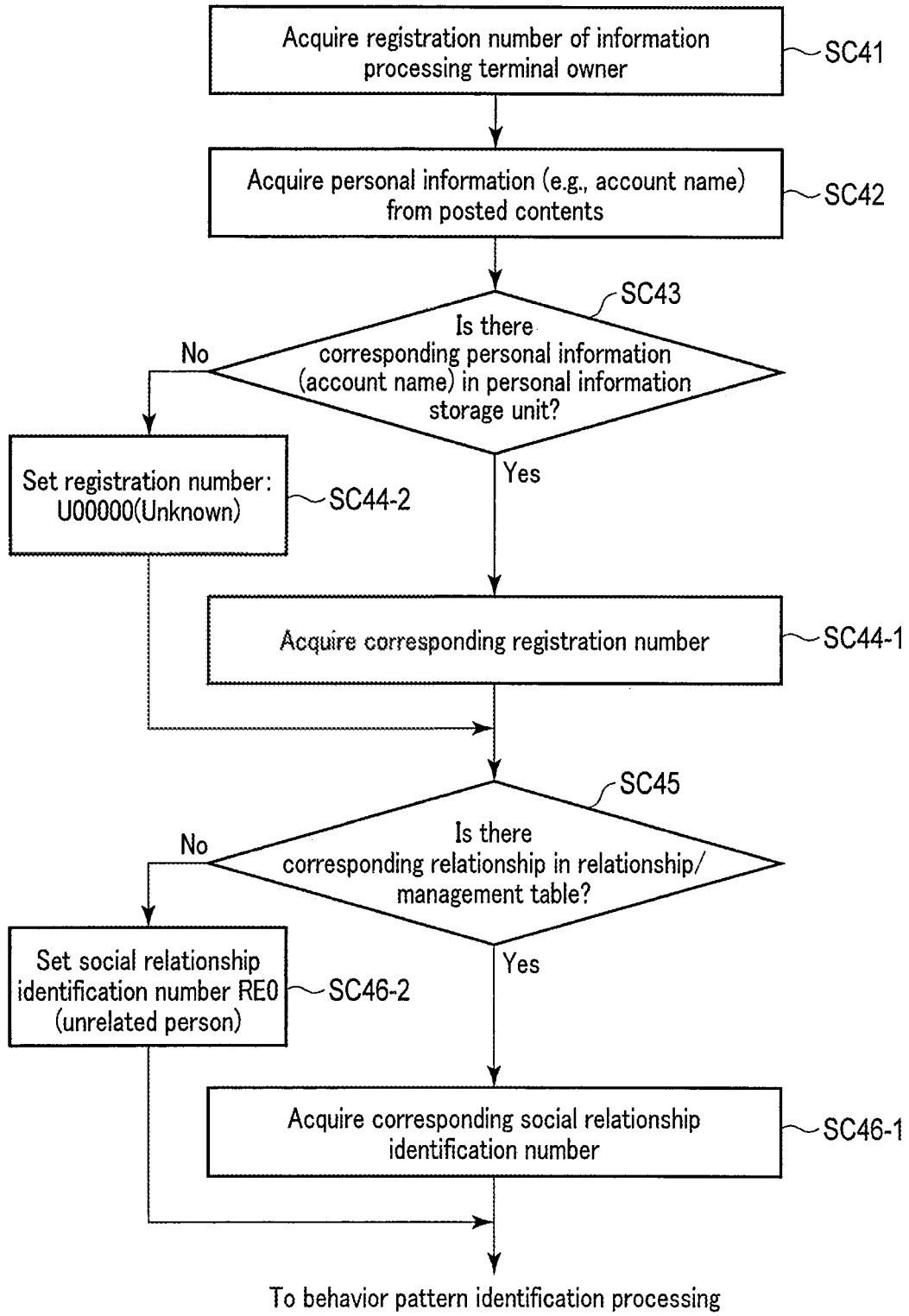
FIG. 33 is a view showing a flow of social relationship identification processing according to Modification 4.

FIG. 33 is a view showing a flow of social relationship identification processing according to this Modification 4. As shown in FIG. 33, a social relationship/social behavior pattern identification function 301 acquires personal information (an account name) of an unrelated person who communicates with a holder of the information processing terminal 2 through the SNS from a registration number "registration number: U0001 (Taro Tokkyo)" and posted contents of the holder of the information processing terminal 2 included in the social behavior information transmitted from the information processing terminal 2 (a step SC41 and a step SC42). Further, the social relationship/social behavior pattern identification function 301 determines whether the personal information (the account name) of the unrelated person acquired at the step SC42 is present in an account management table 311 (a step SC43). As a result of the determination, when the personal information (the account name) of the unrelated person is present, the social relationship/social behavior pattern identification function 301 acquires a registration number corresponding to the personal information (the account name) of the unrelated person from the account management table 311 (a step SC44-1). On the other hand, as a result of the determination, when the personal information (the account name) of the unrelated person is not present, the social relationship/social behavior pattern identification function 301 executes processing on the assumption that "registration number: U0000 (Unknown)" has been acquired (a step SC44-2).

Next, the social relationship/social behavior pattern identification function 301 uses the registration number "U00001" of the measurement target person, the registration number of the other measurement target person acquired at the step SC44, and a social relationship management table 312 (see FIG. 6) to determine whether a defined social relationship is present between these persons (a step SC45). As a result of the determination, when the defined social relationship is present between these persons, a corresponding relationship identification number is acquired by making reference to the social relationship management table 312, and a weight of this relationship is acquired by making reference to a relationship weight management table (a step SC46-1). On the other hand, as a result of the determination, when no defined social relationship is present between these persons, or when "registration number: U0000 (Unknown)" has been acquired at the step SC44-2, a relationship identification number "RE0 (unrelated person)" is acquired (a step SC46-2).

The social behavior pattern identification processing according to this Modification 4 is substantially the same as the flow of the processing shown in FIG. 28. That is, when "address of email sender" and "address of email receiver" in FIG. 28 are replaced by "registration number of holder of information processing terminal 2" and "registration number of poster of SNS communication", respectively and the same processing is carried out, the behavior pattern identification according to this Modification 3 can be realized.

(Modification 5)

As an effective use case of the medical information system 1, there is, e.g., follow-up before and after a medical practice to a measurement target person. That is, the medical information system is used for observation of a change in the follow-up before and after a medical practice or after implementation of a medical practice to the measurement target person. In such a case, at least medical treatment information (a type of a medical treatment, a date and time of the medical treatment, and the like) of the measurement target person, a sociality item corresponding to the type of the medical treatment, and its observation period or a threshold value are stored in storage circuitry 31 of an external server 3 in advance. It is preferable for a sociality measurement function 302 to perform sociality measurement from social behavior provided before and after a medical practice such as a medical treatment, and give notice when a change is observed.

(Effect)

According to the foregoing embodiment, data concerning social behavior or a measurement target person can be collected, a database in which relationships of the measurement target person with others and everyday social behavior based on behavior patterns are quantitated by using this data can be automatically configured, and sociality items based on the reference, e.g., SF-36 or SIP can be evaluated and measured by using results. Consequently, the entire QOL including the social behavior can be quantitatively measured.

When the measurement target person puts on the information processing terminal and lives his/her everyday life without answering special inquiries, the database which is highly objective about the social behavior of himself/herself can be automatically configured. Further, the measurement target person does not have to change his/her a lifestyle habit by using a desired account. Consequently, continuous management of the social QOL which does not impose a burden on the measurement target person can be supported.

Furthermore, when a physician performs feedback to a target person by using measurement results provided by this system, instructions for an improvement in more effective social QOL than conventional examples can be realized. Moreover, when the physician periodically confirms sociality measurement results stored in the external server 3 installed in a hospital, the social QOL of patients can be preferably managed.

Additionally, when the information processing terminal 2 and the external server 3 are separately provided, the information processing terminal 2 has the social behavior information generation circuitry alone and the external server 3 has other structures, many pieces of information required for this information processing system can be intensively managed in the external server 3, and an amount of data which is supported to be provided in the information processing terminal 2 held by each measurement target person can be reduced. Further, when personal information in the registration measurement target person management table, the account management table, and the like is stored in the highly confidential external server 3, the personal information can be safely managed.

Second Embodiment

Figure 34:
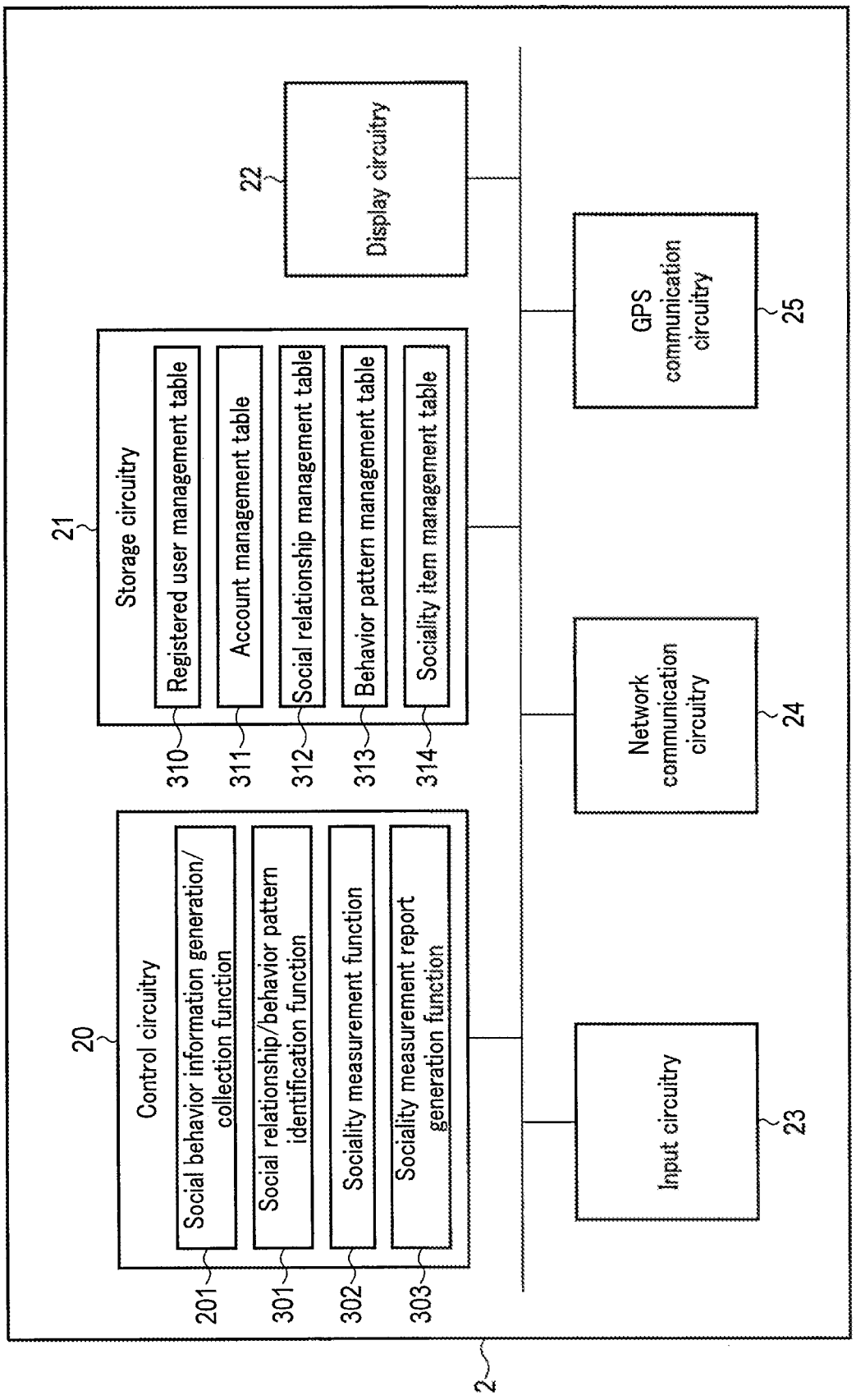
FIG. 34 is a view for explaining a configuration of an information processing terminal 2 according to a second embodiment.

FIG. 34 is a view for explaining a configuration of an information processing terminal 2 according to a second embodiment. A medical information system 1 according to this embodiment realizes, in the information processing terminal 2, generation and collection of social behavior information to processing of sociality measurement (or to generation and output of a sociality behavior report) realized in the medical information system 1 according to the first embodiment. In the information processing terminal 2 in FIG. 34, functions of the social behavior information generation function 200 shown in FIG. 2 and the social behavior information collection function 300 shown in FIG. 3 are integrated in a social behavior information generation/collection circuitry 201, and the information processing terminal 2 comprises social relationship/social behavior pattern identification function 301, a sociality measurement function 302, a sociality measurement report generation function 303, a registered measurement target person management table 310, an account management table 311, a social relationship management table 312, a behavior pattern management table 313, and a sociality item management table 314. Contents of processing realized by each constituent element are the same as those in the first embodiment.

It is to be noted that, as a matter of course, the structures described in Modification 1 to Modification 4 or structures provided by arbitrary combinations of these structures can be applied to the medical information system 1 (the information processing terminal 2) according to the second embodiment.

Furthermore, in case of realizing the structures according to this embodiment in the information processing terminal 2, each function can be configured as a program. In this case, for example, a dedicated application is downloaded to the above-described information processing terminal 2 from a Web page of a company which provides the information service or an Internet store. Each function can be also realized as software by, e.g., operating the dedicated application by a processor incorporated in the information processing terminal 2.

(Effect)

According to this embodiment described above, the measurement of the sociality items can be realized by the information processing terminal 2 alone. A physician or the like can manage the social QOL of the measurement target person by making reference to the measurement results and the like stored in the storage circuitry 21 at predetermined timing, and the effects substantially the same as those in the first embodiment can be realized.

The first and second embodiments have been described above. However, the embodiment is not limited to the first and second embodiments. For example, the information processing terminal 2 may realize at least a part of the functions realized by the external server 3 according to the first embodiment. Further, the external server 3 may realize at least a part of the functions realized by the information processing terminal 2 according to the second embodiment.

The word "processor" used in the description means a circuit such as a CPU (central processing circuitry), a GPU (Graphics Processing circuitry), an application specific integrated circuit (ASIC), a programmable logic device (e.g., a simple programmable logic device (SPLD)), a complex programmable logic device (CPLD), a field programmable gate array (FPGA), and the like. The processor realizes a function by executing reading of a program stored in a storage circuit. It is to be noted that each processor in this embodiment is not restricted to a case where each processor is configured as a single circuit, and independent circuits may be combined to configure one processor so that its function can be realized.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A medical information system comprising:
an information processing terminal used by a measurement target person; and
a medical information server external to the information processing terminal and communicating with the information processing terminal via a communications network,
the medical information server comprising:
a memory that stores at least a social relationship management table in which the measurement target person is associated with others in a social relationship, and a sociality item management table which stores sociality items as Quality of Life (QOL) indexes relating to sociality of the measurement target person in association with the social relationship and a behavior pattern; and
first processing circuitry configured to:
collect social behavior information about the measurement target person from the information processing terminal, the social behavior information including a daily sound of the measurement target person and a daily amount of exercise of the measurement target person, the first processing circuitry being configured to collect positional information as the social behavior information, collect an electronic mail as the social behavior information, collect call contents using a telephone as the social behavior information, or collect posted contents to a social networking service (SNS) as the social behavior information;
identify the social relationship between the measurement target person and the others, by using the social relationship management table and the collected social behavior information;
identify a behavior pattern of the measurement target person, by using the sociality item management table and the identified social relationship, the first processing circuitry being configured to identify the behavior pattern based on the positional information, identify the behavior pattern by analyzing a text of the electronic mail, identify the behavior pattern by analyzing a text of the call contents, or identify the behavior pattern by analyzing a text of the posted contents;
quantitatively measure a sociality item as a QOL index concerning sociality of the measurement target person by using the identified social relationship and the identified behavior pattern; and
generate a sociality measurement report by using a measurement result of the sociality item, wherein
the social behavior information is information relating to communication performed by the measurement target person with the others, and
the behavior pattern is information classified by emotion of the measurement target person; and
output circuitry configured to output the sociality measurement report, the information processing terminal comprising:
second processing circuitry configured to
acquire the daily sound via a microphone, and
transmit, via the communications network, the social behavior information including the acquired daily sound to the medical information server, wherein
the first processing circuitry
acquires a sound volume from the daily sound included in the transmitted social behavior information,
converts the daily sound into a text, and divides the text into words, and
identifies, based on the text, the sound volume, and a threshold value of the sound volume, a further detailed behavior pattern associated with emotion that is represented by the text, and
the memory stores measurement results of sociality items of a plurality of measurement target persons.

2. The system according to claim 1, wherein the social behavior information includes information concerning emotional behavior.

3. The system according to claim 1, wherein the memory stores at least a behavior pattern table in which pieces of social behavior are associated with behavior patterns, wherein the first processing circuitry identifies the behavior pattern of the measurement target person by using the behavior table and the collected social behavior information.

4. The system according to claim 1, wherein the first processing circuitry is configured to:
collect the positional information as the social behavior information; and identify the behavior pattern on the basis of the positional information of the measurement target person and the positional information of the others.

5. The system according to claim 1,
wherein the first processing circuitry is configured to:
collect the electronic mail as the social behavior information; and
identify the behavior pattern by analyzing the text of the electronic mail.

6. The system according to claim 1,
wherein the first processing circuitry is configured to:
collect the call contents using the telephone as the social behavior information; and
identify the behavior pattern by analyzing the text of the call contents.

7. The system according to claim 1,
wherein the first processing circuitry is configured to:
collect the posted contents to the social networking service (SNS) as the social behavior information; and
identify the behavior pattern by analyzing the text of the posted contents.

8. The system according to claim 1,
wherein the first processing circuitry is configured to:
collect social behaviors of measurement target persons including the measurement target person before and after medical practice for the measurement target person;
determine the behavior pattern of the measurement target person by using a social behavior before and after the medical practice; and
quantitatively measure the sociality item of the measurement target person before and after the medical practice for the measurement target person by using the social relationship and the behavior pattern, which is obtained before and after the medical practice for the measurement target person.

9. The system according to claim 1,
wherein the first processing circuitry is configured to quantitatively measure the sociality item of the measurement target person by comparing the social relationship and the behavior pattern, which is previously obtained about the measurement target person with the social relationship and a behavior pattern, which is currently obtained about the measurement target person, with regard to the same sociality item.

10. The system according to claim 1,
wherein the first processing circuitry is configured to quantitatively measure the sociality item of the measurement target person by comparing information of the others based on the social relationship and the behavior pattern, which is obtained about the others with the social relationship and a behavior pattern currently obtained about the measurement target person, with regard to the same sociality item.

11. The system according to claim 1, further comprising a display configured to display the sociality measurement report.

12. The system according to claim 1, wherein the first processing circuitry is configured to output an alert on the basis of the measurement result of the sociality item.

* * * * *